United States Patent [19]
Goldbach et al.

[11] Patent Number: 6,150,585
[45] Date of Patent: Nov. 21, 2000

[54] NUCLEIC ACIDS ENCODING TOSPOVIRUS GENOME AND EXPRESSION THEREOF

[75] Inventors: Robert Willem Goldbach, Bennekom; Dirk Peters, Wageningen; Johannes Jacobus Ludgerus Gielen, Enkhuizen; Petrus Theodorus de Haan, Randwijk; Arnoldus Johannes Kool; Martinus Qúirinus Joseph Marie van Grinsven, both of Enkhuizen, all of Netherlands

[73] Assignee: Novartis Finance Corporation, New York, N.Y.

[21] Appl. No.: 08/757,011

[22] Filed: Nov. 26, 1996

Related U.S. Application Data

[63] Continuation of application No. 08/280,903, Jul. 27, 1994, abandoned, which is a continuation of application No. 08/143,397, Oct. 26, 1993, abandoned, which is a continuation of application No. 08/047,346, Apr. 14, 1993, abandoned, which is a continuation of application No. 07/694,734, May 2, 1991, abandoned, which is a continuation-in-part of application No. 07/446,024, Dec. 5, 1989, abandoned, which is a continuation-in-part of application No. 07/431,259, Nov. 3, 1989, abandoned.

[51] Int. Cl.[7] ............................... A01H 5/00; A01H 5/10; C12N 15/12; C12N 15/82
[52] U.S. Cl. ..................... 800/205; 800/250; 435/172.3; 435/419; 536/23.72
[58] Field of Search ................................ 800/205, 250; 435/5, 6, 172.3, 320.1, 418, 419; 536/23.1, 23.72

[56] References Cited

FOREIGN PATENT DOCUMENTS

| | | |
|---|---|---|
| 223452 | 10/1986 | European Pat. Off. . |
| 240332 | 1/1987 | European Pat. Off. . |

OTHER PUBLICATIONS

Wilson (1993) Proc. Natl Acad Sci USA 90 : 3134–3141.
Lewin (1987) Science 237 : 70.
Nejidat et al (1990) Physiologia Plantarum 80 : 662–668.
Verbleij et al (1983) J. gen virol. 64 : 677–686.
Cuozzo et al (1988) Bio/Technology 6 : 549–557.
German et al. 1988 "Dot Blot Detection of Tomato Spotted Wilt Virus Uing Cloned Complementary DNA Probes" Phytopathology 78:1599.
Ronco et al. 1989 "Cloned complementary DNA probes for the detection of Tomato Spotted Wilt Virus" Phytopathology 79(11):1309–1313.
DeHaan et al. 1989 "Molecular Cloning and Terminal Sequence Determination of the S and M RNAs . . . " J. Gen. Virol. 70:3469–3473.
DeHaan et al. 1990 "The S RNA Segment of Tomato Spotted Wilt Virus Has An Ambisense Character" J. Gen. Virol. 71:1001–1007.
Huguenot et al. 1990 "Detection of Tomato Spotted Wilt Virus using monoclonal antibodies and riboprobes" Arch. Virol. 110(1/2):47–62.
Wilson 1993 "Strategies to protect plants against viruses" Proc. Natl. Acad. Sci USA 90:3134–3141.
Nejidat et al. 1990 "Engineered resistance against plant virus disease" Physiol. Plantarum 80:662–668.
Lewin 1987 "When does homology mean something else" Science 237:70.
Cuozzo et al. 1988 "Viral Protection in transgenic tobacco plants expressing the cucumber mosaic virus coat . . . " Bio/Technology 6:549–557.
Verkleig et al. 1982 "Evidence that Tomato Spotted Wilt Virus RNA is a positive strand" J. Gen. Virol. 48:329–338.

*Primary Examiner*—Elizabeth F. McElwain
*Attorney, Agent, or Firm*—Thomas Hoxie

[57] ABSTRACT

Recombinant DNA constructs comprising a DNA coding for transcription into an RNA sequence of tospoviruses or into RNA sequences related thereto, the use of such DNA constructs to transform plants having reduced susceptibility to tospovirus infection and probes for the isolation of tospovirus or diagnosis of plant tospovirus diseases.

16 Claims, 36 Drawing Sheets

FIG.4

| FIG.4A |
| FIG.4B |
| FIG.4C |
| FIG.4D |

```
  1   AGA GCA AUU GUG UCA GAA UUU UGU UCA UAA UCA AAC CUC ACU UAG AAA AUC ACA AUA CUG met ser ser ser val tyr glu ser ile ile gln
 61   UAA UAA GAA CAC AGU ACC AAU AAC CAU AAU GUC UUC AAG UGU UUA UGA GUC GAU CAU UCA thr arg ala ser val trp gly ser thr ala ser gly lys ala val val asp ser tyr trp
121   GAC AAG AGC UUC AGU CUG GGG AUC AAC UGC AUC UGG UAA AGC UGU UGU AGA UUC UUA CUG ile his glu leu gly thr gly ser gln leu val gln thr gln leu tyr ser asp ser arg
181   GAU UCA UGA ACU UGG UAC UGG UUC UCA ACU AGU UCA GAC CCA GCU GUA UUC UGA UUC AAG ser lys val val leu trp leu tyr cys lys val gly ile phe pro val lys lys lys arg
241   AAG CAA AGU AGU CCU UUG GCU AUA CUG CAA AGU AGG GAU CUU CCC UGU GAA GAA GAA GAG phe leu ser gln his val tyr ile pro ile phe asp asp ile asp phe ser ile asn ile
301   AUU UCU UUC UCA GCA UGU GUA UAU CCC UAU UUU UGA UGA UAU UGA UUU UAG CAU CAA UAU asp asn ser val leu ala leu ser val cys ser asn thr val asn ala asn gly val lys
361   UGA UAA CUC UGU UCU GGC ACU AUC UGU UUG CUC AAA UAC AGU CAA UGC UAA CGG AGU GAA his gln gly his leu lys val leu ser pro ala gln leu his ser ile glu ser ile met
421   ACA UCA AGG UCA UUU GAA GGU UUU GUC UCC UGC CCA GCU CCA CUC UAU UGA AUC UAU CAU asn arg ser asp ile thr asp arg phe gln leu gln glu lys asp ile ile pro asn asp
481   GAA CAG AUC UGA UAU UAC AGA CCG AUU CCA GCU CCA AGA AAA AGA CAU AAU UCC AAU UGA lys tyr ile glu ala ala asn lys gly ser leu ser cys val lys glu his thr tyr lys
541   CAA AUA CAU UGA AGC UGC AAA CAA AGG CUC UUU GUC UUG UGU CAA AGA GCA UAC CUA UAA ile glu met cys tyr asn gln ala leu gly lys val asn val leu ser pro asn arg asn
601   GAU CGA GAU GUG CUA UAA UCA GGC UUU AGG CAA AGU GAA UGU UCU AUC UCC UAA CAG AAA val his glu trp leu tyr ser phe lys pro asn phe asn gln val glu ser asn asn arg
661   UGU CCA UGA AUG GCU GUA CAG UUU CAA GCC AAA UUU CAA UCA AGU GAA AAG CAA CAA CAG thr val asn ser leu ala val lys ser leu leu met ser ala glu asn asn ile met pro
721   AAC UGU AAA UUC UCU UGC AGU GAA AUC UCU GCU CAU GUC AGC AGA AAA CAA CAU CAU GCC asn ser gln ala ser thr asp ser his phe lys leu ser leu trp leu arg val pro lys
781   UAA CUC UCA AGC UUC CAC UGA UUC UCA UUU CAA GCU GAG CCU CUG GCU AAG GGU UCC AAA val leu lys gln val ser ile gln lys leu phe lys val ala gly asp glu thr asn lys
841   GGU UUU GAA GCA GGU UUC CAU UCA GAA AUU GUU CAA GGU GCA AGG AGA UGA AAC AAA CAA
```

FIG.4A

```
           thr  phe  tyr  leu  ser  ile  ala  cys  ile  pro  asn  his  asn  ser  val  glu  thr  ala  leu  asn
901        AAC  AUU  UUA  UUU  AUC  UAU  UGC  CUG  CAU  UCC  AAA  CCA  UAA  CAG  UGU  UGA  GAC  AGC  UUU  AAA ile  thr  val  ile  cys  lys  his  gln  leu  pro  ile  arg  lys  cys  lys  ala  pro  phe  glu  leu
961        CAU  UAC  UGU  UAU  UUG  CAA  GCA  UCA  GCU  CCC  AAU  UCG  CAA  AUG  CAA  AGC  UCC  UUU  UGA  AUU ser  met  met  phe  ser  asp  leu  lys  glu  pro  tyr  asn  ile  val  his  asp  pro  ser  tyr  pro
1021       AUC  AAU  GAU  GUU  UUC  UGA  UUU  AAA  GGA  GCC  UUA  CAA  CAU  UGU  UCA  UGA  CCC  UUC  AUA  CCC lys  gly  ser  val  pro  met  leu  trp  leu  glu  thr  his  thr  ser  leu  his  lys  phe  phe  ala
1081       CAA  AGG  AUC  GGU  UCC  AAU  GCU  CUG  GCU  CGA  AAC  UCA  CAC  AUC  UUU  GCA  CAA  GUU  CUU  UGC thr  asn  leu  gln  glu  asp  val  ile  ile  tyr  thr  leu  asn  asn  leu  glu  leu  thr  pro  gly
1141       AAC  UAA  CUU  GCA  AGA  AGA  UGU  AAU  CAU  CUA  CAC  UUU  GAA  CAA  CCU  UGA  GCU  AAC  UCC  UGG lys  leu  asp  leu  gly  glu  arg  thr  leu  asn  tyr  ser  glu  asp  ala  tyr  lys  arg  lys  tyr
1201       AAA  GUU  AGA  UUU  AGG  UGA  AAG  AAC  CUU  GAA  UUA  CAG  UGA  AGA  UGC  CUA  CAA  AAG  GAA  AUA phe  leu  ser  lys  thr  leu  glu  cys  leu  pro  ser  asn  thr  gln  thr  met  ser  tyr  leu  asp
1261       UUU  CCU  UUC  AAA  AAC  ACU  UGA  AUG  UCU  UCC  AUC  UAA  CAC  ACA  AAC  UAU  GUC  UUA  CUU  AGA ser  ile  gln  ile  pro  ser  trp  lys  ile  asp  phe  ala  arg  gly  glu  ile  lys  ile  ser  pro
1321       CAG  CAU  CCA  AAU  CCC  UUC  AUG  GAA  GAU  AGA  CUU  UGC  CAG  AGG  AGA  AAU  UAA  AAU  UUC  UCC gln  ser  ile  ser  val  ala  lys  ser  leu  leu  lys  leu  asp  leu  ser  gly  ile  lys  lys  lys
1381       ACA  AUC  UAU  UUC  AGU  UGC  AAA  AUC  UUU  GUU  AAA  GCU  UGA  UUU  AAG  CGG  AUC  AAA  AAA  GAA glu  ser  lys  val  lys  glu  ala  tyr  ala  ser  gly  ser  lys  OCH
1441       AGA  AUC  UAA  GGU  UAA  GGA  AGC  GUA  UGC  UUC  AGG  AUC  AAA  AUA  AUC  UUG  CUU  UGU  CCA  GCU 1501       UUU  UCU  AAU  UAU  GUU  AUG  UUU  AUU  UUC  UUU  CUU  UAC  UUA  UAA  UUA  UUU  CUC  UGU  UUG  UCA 1561       UCU  CUU  UCA  AAU  UCC  UCC  UGU  CUA  GUA  GAA  ACC  AUA  AAA  ACA  AAA  AAU  AAA  AAU  GAA  AAU 1621       AAA  AUU  AAA  AUA  AAA  UAA  AAU  CAA  AAA  AUG  AAA  UAA  AAA  CAA  CAA  AAA  AUU  AAA  AAA  CGA 1681       AAA  ACC  AAA  AAG  ACC  CGA  AAG  GGA  CCA  AUU  UGG  CCA  AAU  UUG  GGU  UUU  GUU  UUU  GUU  UUU 1741       UGU  UUU  UUG  UUU  UUU  AUU  UUU  UAU  UUU  AUU  UUU  AUU  UUA  UUU  UAU  UUU  UAU  UUU  AUU  UUU 1801       AUU  UUA  UUU  AUU  UUU  UGU  UUU  CGU  UGU  UUU  UGU  UAU  UUU  AUU  AUU  UAU  UAA  GCA  CAA  CAC
```

FIG.4B

```
1861 ACA GAA AGC AAA CUU UAA UUA AAC ACA CUU AUU UAA AAU UUA ACA CAC UAA GCA AGC ACA

1921 AGC AAU AAA GAU AAA GAA AGC UUU AUA UAU UUA UAG GCU UUU UUA UAA UUU AAC UUA CAG

1981 CUG CUU UCA AGC AAG UUC UGC GAG UUU UGC CUG CUU UUU AAC CCC GAA CAU UUC AUA GAA
     OPA ala leu glu ala leu lys ala gln lys lys val gly phe met glu tyr phe 2041 CUU GUU AAG AGU UUC ACU GUA AUG UUC CAU AGC AAC ACU CCC UUU AGC AUU AGG AUU GCU
     lys asn leu thr glu ser tyr his glu met ala val ser gly lys ala asn pro asn ser 2101 GGA GCU AAG UAU AGC AGC AUA CUC UUU CCC CUU CUU CAC CUG AUC UUC AUU CAU UUC AAA
     ser ser leu ile ala ala tyr glu lys gly lys lys val gln asp glu asn met glu phe 2161 UGC UUU GCU UUU CAG CAC AGU GCA AAC UUU UCC UAA GGC UUC UUU GGU GUC AUA CUU CUU
     ala lys ser lys leu val thr cys val lys gly leu ala glu lys thr asp tyr lys lys 2221 UGG GUC GAU CCC GAG GUC CUU GUA UUU UGC AUC CUG AUA UAU AGC CAA GAC AAC ACU GAU
     pro asp ile gly leu asp lys tyr lys ala asp gln tyr ile ala leu val val ser ile 2281 CAU CUC AAA GCU AUC AAC UGA AGC AAU AAG AGG UAA GCU ACC UCC CAG CAU UAU GGC AAG
     met glu phe ser asp val ser ala ile leu pro leu ser gly gly leu met ile ala leu 2341 UCU CAC AGA CUU UGC AUC AUC GAG AGG UAA UCC AUA GGC UUG AAU CAA AGG AUG GGA AGC
     arg val ser lys ala asp asp leu pro leu gly tyr ala gln ile leu pro his ser ala 2401 AAU CUU AGA UUU GAU AGU AUU GAG AUU CUC AGA AUU CCC AGU UUC UUC AAC AAG CCU GAC
     ile lys ser lys ile thr asn leu asn glu ser asn gly thr glu glu val leu arg val 2461 CCU GAU CAA GCU AUC AAG CCU CCU GAA GGU CAU GUC AGU GCC UCC AAU CCU GUC UGA AGU
     arg ile leu ser asp leu arg arg phe thr met asp thr gly gly ile arg asp ser thr 2521 UUU CUU UAU GGU AAU UUU ACC AAA AGU AAA AUC GCU UUG CUU AAU AAC CUU CAU UAU GCU
     lys lys ile thr ile lys gly phe thr phe asp ser gln lys ile val lys met ile ser 2581 CUG ACG AUU CUU UAG GAA UGU CAG ACA UGA AAU AAC GCU CAU CUU CUU GAU CUG GUC GAU
     gln arg asn lys leu phe thr leu cys ser ile val ser met lys lys ile gln asp ile 2641 GUU UUC CAG ACA AAA AGU CUU GAA GUU GAA UGC UAC CAG AUU CUG AUC UUC CUC AAA CUC
     asn glu leu cys phe thr lys phe asn phe ala val leu asn gln asp glu glu phe glu 2701 AAG GUC UUU GCC UUG UGU CAA CAA AGC AAC AAU GCU UUC CUU AGU GAG CUU AAC CUU AGA
     leu asp lys gly gln thr leu leu ala val ile ser glu lys thr leu lys val lys ser
```

FIG.4C

2761 CAU GAU GAU CGU AAA AGU UGU UAU AUG CUU UGA CCG UAU GUA ACU CAA GGU GCG AAA GUG
     met 2821 CAA CUC UGU AUC CCG CAG UCG UUU CUU AGG UUC UUA AUG UGA UGA UUU GUA AGA CUG AGU

2881 GUU AAG GUA UGA ACA CAA AAU UGA CAC GAU UGC UCU

FIG.4D

1   AGAGCAAUC. .......... .......... ..........
    .......... .......... .......... ....CAUAGA
    UCAUCAAAUA ACUUAUAUGC GAAGAUUCUG UGCAACAGUU
    UGCUAAAUGC CUGCAAUAGA GAGGAAUAAU CGCUCCAUUU
    ACUAAUUCUU UCAGAUAUAA ACUCUACUUC UGAUGAAGAA
    GCAUAACUCU UUUUUGGGUU CAAAGUUAUG CAAAAACUUU
    UGAAAUGAGC UUCAAUGCUU CUAAACAACA UUUCUGGCAG
    AGAUGAGCUU GAAAGUCUG UCAGCAUUUU AUCAACCUCU
    CCACUGGCUA UUAAUGAUGU UGCAUUAUCA UCAGAGUGCA
    CGAUCCAUCU AGUUUGGAAA UCACAGUUUU UGUAACAUUC
    CAAAGUCUUG UGAUAAGCUU UCAUUGCACG AGAGUGAUAA
    ACGGAAGACA GAUAAUUUAA AUUGCCUUGC AACCAAUUCA
    UGCUAACAGG GUAUGUGUUU GUCGUCGAGC CUUUGGUCGA
    AAGUCCUAUG GCAGUUUCAU UUUGCCCAAA AGUUUCUUGA
    GCUUUUCUUA GAUUCAAAAA AAUAUCUGUU GGUAUACAAA
    CCUUCUUCAA UUUAACAUAC AUUAGAAUCU UGAUGUAUUG
    AUUGCUCU (app. nt 5000)

| FIG. 6B-1 |
| FIG. 6B-2 |
| FIG. 6B-3 |
| FIG. 6B-4 |

FIG. 6B-1

```
   1  AGAGCAAUCA GGUACAACUA AAACAUAUAA CCUCUCCACA GCCAGACUUU ACAAAUUACA    60
  61  UAAGAAUUCC CUCCAGUGAA ACUAUACGG GACUCUACAU UUAUAUACAC UAUAGAUUUG    120
 121  GUUCACCAAA UUGUUUUAGG CUAAUCUAAU CUAAUCUAAU AG CAAUAAUUU             180
 181  AUAUUCUAAG UUAUAUCUAA UCUGUUAUUC AUGGAUUGUU AGUCAUUACU UUCAAUUUAA    240
 241  UCUGUGUCUU CUUCCUCAUC AGCUCACUCU CAUCAAAGG CAUCUUCUUC CCCUCUUAGA    300
 301  UAACUAAGCA AGAAAUUGCU UUCAUCUGUU UCAACAACCU CGUCCAACUC ACUAUUUUUA    360
 361  CUCAAAAUAA UCUCUCUGU UUGCAUGAUA UAACAUUGA UAUCAGAGUA GGUAUAUCUU    420
 421  CCAUACAAUG UUUUUUUCUGA UAAACAUAGU GGGUGCCUAG CAAGGAAAUU UGCGAUAUCC    480
 481  UUAUAGACCU CUAGUUUUUU AGUCGCGAU UGUUCACUC UUAAUUGUAU CAAAGCUUUU    540
 541  UUAACUCUUC CAGACAAGAA AUGUUCCUUG GACCUGCUUU UUGUCAGUUU UAGAUAACCU    600
 601  UCUAAGCUGU CAGUCACUGU AUUUAAAGGA CAAUGACAAU UCUAUAUUC CAUAUAAACA    660
 661  GUUGCAUAAA CUUUGAGUGC AGGUACACUG GAACUUAAAC UUCCCAAUCU GUCAGUUGAA    720
 721  AAUAGUCUG GUCUAAAACU GUCAACUCUA AAGUCUCUA UAUCAAAGCU GGUUCCCUUU    780
 781  AUCCUCCAA UCAAGAACUU AAUUUCCUUUU UCUUGAUCA AGACUUCAUA UAUCAAGCU    840
 841  AACCCUUUCU UCAACACAUU AAAACUGGCA CCAUUUUCU AGACCCACAA AUUCUCAUC    900
 901  UCACUCUAAG UCUCUCCAGA UAUAACAAAC CCAUUUGCAGU GUCUAGAUAGU CCUAGAUAGU    960
 961  AUUUAAGAU UAUUUUGCA CAAACCAGC GCUUGGAAAG CAUAACUUUU UUCCAUUUAG    1020
1021  UCGAAUAAU AGUCAGAU AGUCCUUAA AGUACCAUU CAUAACCUUC GGCAUGUGC    1080
1081  UGGUUUGCA CAUUCCAGA CUGCUUAAG GAUCUAUAG UCCCAAAGU GUGGAUGUU    1140
1141  CUGCAAGAA CAUUCCUUAA AGUCCAAUG GAUCCAUU AGUCCCUAU CUCUAUGUCCAU    1200
1201  UCACAAGCUU UAACAAGG AGCAUGCAAC AGCAGAGU AAUCCCAU AAAUCCUGAU    1260
1261  UUUUUGCCA UUAGAGAAUA UUUAAGCAUG UUAGCCUC UAAGCUUU UCUAAAUCU    1320
1321  GCAUCAUUUA UUAGAGAAUA UUUAAGCAUG UCAGUAUUU CUUGAAACC CUCAAAUCU    1380
1381  CUAGUAUACU GUUUCUAG GUCAACAAU UCUGAAAAA GAGGACUAUA CUCAUUUCA    1440
1441  AAGUGUCAU GUGUCUUAG CAAGUUCUA AAUAGUUCUA CUGUGUCAGU AAAUCCAUUU    1500
1501  UCAUCAAGAU AGCUACAUA UCUUCCACA GAAUUUCAGU CUUUGCAGU UUCCAAACC    1560
1561  GUAUCCCGA UGUUCAUUAA GAAUCAUUU CAAUGCAGU UGAUCAUC AUCUACAAUC    1620
1621  UCUUGAUCU GCUGUGAUAA GUUUCAGUU GUUUCCAAAG AGUUUCUC AGUCAUAAGC    1680
1681  CUGUUUUUUA UGGUUUGAU UGUUCAGGU UGUUCAGU GCUUCAGAGAG CAUAUCAGAG    1740
1741  AAAAAUCCC CUACUUCAGG GAGCCUUAAG UUCAUAUUUU CAGUUUUAUA UUUGGCUUUC CUAAAUUACU UAUAAUUACU    1800
1801  CAUACAUCGG AAUUCACAU AUUAAUUUA UUCUUUACAA AUCUUAACAA CUAAUUCUU CUAAUCCAGAU AUCCUUCCGG    1860
1861  CUAUUUGUC UUGAUGUAGC CUAGUUUCAC UGAUGUAGU ACAAUCUUUU UGUGGCUUG UGUCUCUG    1920
1921  AUGCAAGAUC UCCGGUUCU AGAAAACAA UCUGGGUUCU UAUGAUUUAU UUUGAUUUAU UAUGUUCACU    1980
```

FIG. 6B-2

```
3961  ..........  CCAAGCUUGU  UAAAAAUUCU  AAUACUAUCA  UUCACUUCAC  CAGGAAGCAU  UGAAUAGAUG  4020
4021  CUUAAUGCUU  GUACCUGCAC  AGCCCCAUAA  AUGUAUACUG  GCAAAAGGUA  UAACUUCAUU  AGGACAGCCU  4080
4081  UUUCUCAGAA  GCAUGUAAC   AUGUAUACUG  GUUUGCUAAA  UGCCUGCAAU  GAUCAUCAAA  AUAACUAUAA  4140
4141  UGCGAAGAUU  CUGUGCAACA  GUUUGCUAAA  AACUCUACU   UCUGAUGAAG  AGAGAGGAAU  AAUCGCUCCA  4200
4201  UUUACAAUUC  UUUCAGAUAU  AACUCUACU   UUUGAAAUGA  AAGCAUAACU  AGCAUAAACU  CUUUUUGGG   4260
4261  UUCAAAGUUA  UGCAAAAACU  UUUGAAAUGA  GCUUCAAUGC  UUCUAAACAA  AAGCAUAAGC  CAUUUCUGGC  4320
4321  AGAGAUGAGC  UUGAAAAGUC  UGUCAGCAUU  UUAUCAACCU  CUCCACUGGC  UAUUAAUGAU  4380
4381  GUUGCAUUAU  CACAGAGUG   CACAAUCCAU  CUAGUUUGGA  AAUCACAGUU  UUUGUAACAU  4440
4441  UCCAAGUGU   UGUGAUAAGC  UU........  ..........  ..........  ..........  ..........

..........  ..........  ..........  ..........  ..........  ..GAAUUGC
      AUCAUGUCUU  CAGAGAUAAG  GUAAAUGGCU  AGAUCAUUGC  AUAAUUGUU   UAUCUUUUUG
      CAAGUCUCUA  AUCAGUCUU   CAGUACGAA   UCUUGAAUGU  ACAAGCAUUC  AGUAUUUUUA
      GCAAAUUAUU  UGAAAACAGA  UGUGAUCUUA  CCAUCUCUA   UUAUAUUAAA  AUAUGAAGU
      AGAAAAAAAG  AGCCCUUAAA  UCUUUACCA   CUUAAGCUAU  CAUCAUUGUC  AUGCCUAUC
      AGUUUUUUCA  UAUGAGUCAG  AGAAGACAUG  UCUAUACUG   AGUAAUCAUC  AUUGGGUCA
      GCCUGCCUUU  CAGAGGUAUC  AGAAUCCAAG  CCUUUAGAGA  UCCUUUCUU   UAUUUCUUCU
      UUUUUUAGAA  UUCUUUUUCU  AGAACUCAUU  AUAUUCAAAU  UUACUGCUAA  GCCUUUAAAA
      UAGGUAGUU   UGUUCUCCCU  GCCUAGUACU  CCAUCUUUA   AUUCAUUUU   GUUUCUGGU
      AAACACGAAC  CUUGCUAUU   CCAUUCUAU   GACUUUUUG   UCUCUCAAC   UUUGAUACUC
      CCGUGUUUA   UAUCUAUUUC  AUCUAACUAAG  UCCUGCUUUU  CCAUUUCGU   UGUAUCACAA
      CUAGCUCUG   CUAAACACAG  UCUAACUAAG  UUUGUUAUAU  CUCUUGCUUU  AUUGUUUGG
      UAUUAUGC    UACUAUAUGG  GCUAUUAUAU  AUAACCCUG   AAGAACUUUU  GAAGCUCUCC
      CGAAAUUUGC  UAAUAAUGC   GUUGUAGUAA  UCUACCUCUG  AGCUCAAUUC  UAUCUUCAAA
      CUGGGACCA   AGUCAGUGA   AGUUAGUUU   AGUCAGAGA   UGGUUAUGUC  ACAGUAGGA
      UACCUUUCUU  CAUAUUCAGC  AGCAUUCUGG  UUAAAAGCUG  UCUCAAGGUG  AGGUAUCUCU
      UUUCUUUUC   UUUUUUCUA   UCUAAAUUCUA  AGCAUGAUCU  UCUCAAGGUG  UUUUCCAUAC
      AGAGAUUCC   AUAUUGCUG   CUUUGGACC   AAGUGGUCUU  UCAAACAGC   UAAAUCAGCU
      UUUGGCUCUA  UUUUUAAAUU  GAUACAGAG   AAGUGGUACC  CUUUAAAUUU  UAAAUCAGCU
      UGCUGGUCAU  UCAUUGUUUC  AAUGUGGAAA  UUUUGGUACC  CUUUAAAUUC  GUCAGCUAUA
      UCCUCUCUAG  GGAUUUUCAU  CAGAGGAUU   AAUGUGGAAA  CAAACAAAA   AUGUAUUAUU
      UAGGCUAUCU  CAGAGGAUU   UGUAACAAGU  UGUAACAAGU  UUCUUUCAU   AUCUUCGGAA
      UCUUUAGAUC  CAAAUCAUC   ACCUAAGAUU  CCCUGACUU   UAUUUGCUGG  UCCAGUGACU  CCAGUGACU
```

```
UUUGCAUAAU AGUUCUCAC CACUGUGGGU GUGGUUCCAA CUAUUUGCCC AACAUAAGAA
AUAUUUAGCA AUUGGCAUU UUUAGCAUGC UUUAUUCUUU CUCCGUGCAA UGCUGAUGGA
GAACUUCGA AUUUCUCCAA AACCCUGCUA CUAGUAACAG UGAUUGGCAU CCCAGCAAUA
GGUUUCAAUA UAACUAUAGA ACGAAAACA GGAUGCUCUU CCAGGAAUGG CUUUCCAUUC
ACUUUAUAU CUUUGAAAGA UUUCCAAAUA UUCUUGUAGG UAUUUCUCCA UGUUUGGUU
UCAGUCCUGG CAUCGACAGA UAUUUUCCAA UCAUAAAUGA UUAAACAAAG CUCACUGUUU
UUUGAUUCUU UAUAUAUCAC AUAGUAUCA GGGGUGGCAU UAGUGCUAC AUAUUCUUA
UUUAUUCUCU CAAACUCAUC AUCAGAGAGC UUGUUAAUGC AGGACUUUUU GUUGAGUUCA
UCCAGAUAUU CUCUAGUGC AUGCUCUAUC UCCACUUCAU UUCUUUGUUU GGGCUUUAUU
CUAGGGUGCC UGGAGAUCAG CUCUCCAAAA AUGUCAUGCC UUGCUAACUC UGUUUCUAGG
UAUUUUGCU CAAACAGAGA GACCAUCUCA CUUAGCUUUU UUGCAUCCAC AGUUGCCAUC
CCUUUGUUA GUCCUUCACC AUUUGACAA AUUUGACAA UAAACUCUCU CAUGUCUCA
UAAUUUUUG CAUUAUUAU UAUAAUCACA UCUUCUGGGA UUAACUCUCU AUUCUCUUA
UGUAAAUCCA AGCUAGAUC GUGGUUAGAA CCUACACAAU CCUCAAUAGA CAACAGUAAA
GUGGUUCCAU UUUCUAUUAA UUUUUGUAUU UUCUGGAUGU UCAUGUUUGC UUAAAAUCGU
UGUUACCUGA UUGCUCU (app. nt 7500)
```

FIG. 6C-1

```
   1 AGAGCAAUCA GGUACAACUA AAACAUAUAA CCUCUCCACA GCCAGACUUU ACAAAUUACA   60
  61 UAGAAUUCC  CUCCAGUGAA ACUAUACCGG GACUCUACAU UUAUAUACAC UAUAGAUUUG  120
 121 GUUCACCAAA UUGUUUUAGG CUAAUGAAU  CUAAUCGAAU UCUAAAAUAG CAAUAAAUUU  180
 181 AUAUUCUAAG UUAUAUCUAA UCUGUUAUUC AUGGAUUGUU AGCAUUACUU CCCAUUAUAA  240
 241 UCUGUGUCUU CUUCUUCAUC AAGCUCAUCU UCAUCAAAGG CAUCUCUC  CCCUCUAGA   300
 301 UAACUAAGCA AGAAAUUGUC UUCAUCUGUU UUGCAUAGUA UCAACAACCU CGUCCAACCU ACUAUUUUA  360
 361 CUCAAAUAA  UCUCUCUGU  UUGCAUGAUA UAAACAUUGA UCACAGAGUA AUCAGAGUA  GGUAUAUCUU  420
 421 CCAUACAUG  UUUUUCUGA  UAAACAUAGU GGGUGCCUAG CAAGGAAAUU UGCGAUAUCC  480
 481 UAAUAGACCU CUAGUUUUU  AGUACGCGAU UGUCACUCUC UUAAUUGUAU CAAAGCUUUU  540
 541 UUAACUCUUC CAGACAAGAA AGUUCCUUG  GACCUGCUUU UUGUCAGUUU UAGAUAACCU  600
 601 UCUAAGCUGU CAGCUAUCUC AAUGAAAGGA CAAUGACAAU UCUAUAUUC  CAUAUAAACA  660
 661 GUUGCAUAAA CUUUGAGUGC AGGUACACUG GAACUAAAUC GAACUAAAUC UUCCCAAUCU GUCAGUGAA  720
 721 AAUAUGUCUG GUCAAAAACU GUCUAACUCA AAUGUCUCUA UACUAAAGCU GGUUCCCUUU  780
 781 AUUCCUCCAA UCAAGAACUU UAUCAACUCA CUUAGUAGAA GUGUUUUGC  UGGAAAUAAA  840
 841 AACCCUUUCU UUUUCCUUU  AAUUUCCAUU UCUUUGAUCA AACCUCCACA CAUUCUUCC  900
 901 UCAUCUAGCC UCAACACAUU AAAACUGGCA AGACCCACA  CCAUUUUCUU AGACUAUGU  960
 961 AUUUUUAGAU UCUCUCCAGA UAUAAAAAAC CCAUUUUCUU UCAGUAUAGU CCUAGAUAGU 1020
1021 UCUGAUAAAU UUAUUUUCUG UAAAACCAGC GUCUUGAAAU CAUAACUUUU UUCCAUUAAG 1080
1081 UUGUUUUGCA AGUCCAGAUC AUGCUAAU   CUUAUUCUCC UCCCAAAUGU GGCCAUAUGU 1140
1141 CUGCUAAGAA CAUUCCUUAA UAACAAUUG  UUUAAUAUAG AGCAUGUGUU GUGGCAUGUU 1200
1201 GCACAAGCUU UAAUCAACCU GAUCCAUU   AACAGUUGA  AUCCCCUAU  CUCUAUGUGC 1260
1261 UUUUUUGCCA UUAGCUCAAC AGCAUGCAUG CCAUGACAUU UAUAGCUCUC CUCUAGAGAG 1320
1321 GCAUCAUUUA UUAGAGAAUA UUUAAGCAUG AGCAGCAUUG CUUGGAAACC AAAUCCUGAU 1380
1381 CUAGUAUACU GUUUGGCUUU GUCAACAAUC UCUGAAAAAAA GAGGACUAUA CUCUAAAUCU 1440
1441 AAGUGUCAU  GUGUCUUAG  CAAGUUUCG  CUGUGUCAU  CUGUGUCAUU AAAUCCAUUU 1500
1501 UCAUCAAGAU AGCUAUCAUA UGUUCAUUAA AUCCUCCACA AUCGUUUCUC UUCUAAGCAG 1560
1561 GUAUCCCGGA UGUCAUUAA  GAAUUCAUC  AUGUUUCUC  UGAUAUCAUC AUCUACAAUC 1620
1621 UCUUUGAUCU GCGUGAUAA  GUUUCAGGAU GUUUCCAAAG GCUUCUAGGU AGCAUAAGC  1680
1681 CUGUUUUUA  UGGUUUUGAU UGUUUCAGUU UGAUUCAGGU UCAGAGUCUG CAUAUCAGAG 1740
1741 AAAAAUCCC  CUACUUCAGG GAGCCUUAAG ACUAGAGAUU UUUGGCUUUC CAUAUAUCU  1800
1801 CAUACAUCGG AAUUCACAUU UCUAUAUUUU ACUUUAACAA CUAAUUUUAC AUCUCUAGU  1860
1861 CUUAUUUGUC UUGAUGUAGC AAUCACAUU  ACAAACAUUU UGUGUCUGU  GGCAUCUAGU 1920
1921 AUGCAAGAUC UCCUGGUUCU AAGAAAACAA UCUGGGUUG  UUUGAUUUAU UAUGAUUUAU 1980
```

FIG. 6C

| FIG. 6C-1 |
|-----------|
| FIG. 6C-2 |
| FIG. 6C-3 |
| FIG. 6C-4 |
| FIG. 6C-5 |

| | | | | | |
|---|---|---|---|---|---|
|1981|UUAUCAAACA|UAAUUCUGC|CAAUAAUUUC|UCUAUACUUU|CUCUGUAUGU|GUCAAAAGA|2040
|2041|UACUCUCUUU|CAUUCAAUAU|CUCAAAUGGU|GUUCUCAAAG|AAACUGCUAC|AUCUUGAUCA|2100
|2101|GAUGCUAUCA|AUCCCACAUA|GCAGCUUCUU|CUAUGAUCC|CUAUUUUGUA|CAUAGUUCCA|2160
|2161|GAGACAUAAU|UCCUGAUUC|AUCUUGUUCU|UCAGUUUUUA|CAUAUCUUAC|AUCCCUCUU|2220
|2221|CUAAUAUACC|UGAUAACAAA|AUCUAAAUGUU|CUGUGAGAAC|ACAAACCCAU|GUUCCACAUC|2280
|2281|CAGACAAUUU|GUUUCUGGAU|UGUGUUCAAU|CUACUGUUAU|GUGAUAGAAU|CACAUUGAC|2340
|2341|ACUGUGAAGC|CACUGCUGU|UGAAUGUA|AUCUUUUCA|UUUGUCUUC|UAGACUCUGC|2400
|2401|CAUAUAGGUU|UACUGUCAAG|GCAAACAUUU|UGCAAUAUUA|AACUAUAUC|CUCUCUUGUA|2460
|2461|AUUGUGGGA|AAAUGUACUG|CAAUUAUCU|GAUAUGUAUA|CAGCAGUGUC|CAGUAUUUUC|2520
|2521|UCUAAGUUCA|UAUCUUGCUG|AGCACUUACC|ACAGUUCUGA|UAGUUUUGUC|UAAUUAUAUA|2580
|2581|CUAGCUGUAG|AAACAAAAUG|AUAGGAUUCU|UCUUUACUGU|AGAUGGUGGA|UAGGAGAGCU|2640
|2641|AAUGUGUUUG|AGAUAAACCC|UCUCCCUAGA|UUGAACUGUG|AAUAUAAGGG|AAUAGAAGGG|2700
|2701|CUAGUAAAGC|AUGUGUAAUU|UGCUAAAAGC|CUGUUUUGUG|CUGCUAUCAU|AUAAUUGCAU|2760
|2761|GCUUUCACCA|AUCUUUGACA|UUCAUUAGAA|UUGCUAAAAG|CCUCUGUUUC|GAAGCUGUCU|2820
|2821|UGGCCAUUAA|CUAGGGAUUU|UACAUCUCCC|AUGAUUUGUC|CUGCUUUGUU|CGUGCUUGUU|2880
|2881|AAAACAUUAA|UACUAGCUGC|UGUUAGAGGG|AGUUUUUUA|AACCUAAGUU|CUCUAUAUA|2940
|2941|UUUGAUCCAU|AGACAGCAUG|CAUUACUACU|AGUCCGGAG|AGCCUUGGAC|AACAGGUAC|3000
|3001|CAUCUCUCAG|UCUGAAACCA|CCUGAAAAUG|UAGUAUCUC|UUUCCUAGA|UUCACCAAGGG|3060
|3061|UAUGCAGAAU|CUAAAUAUGG|CUAAAUAUGG|AAUCAGCAUG|CAUCCUUGAU|AACUAGAUU|3120
|3121|ACACAGUUU|UAAAUGAACA|AUAUGAAUCU|CUGAAAUAA|CAUCAAAAU|UAGAUUUUC|3180
|3181|UUUCCAUGU|UUUCUUCAUA|AGCAUCUUC|ACAUGUUAAG|AAAUGUUAAC|AAAUGUUCUA|3240
|3241|GCUUUUGAC|UUAACACUCU|AUCUAAAGCA|AGUUUCUCUG|UAGAUUGGGU|CGAUAACUGG|3300
|3301|UUCUUUUAG|AGGGCUUGU|GUACAUGAAC|AGCUGACUAA|GUAAAAAAUC|UCUAUCAUUC|3360
|3361|AAUGGUGCUA|UCAGAAUUGU|UUCAGGAUUU|UUCAGGAUUU|UGUCAUGGAC|AGAUUCCAUU|3420
|3421|UCUAAGCUAG|AUGCAAUCUU|CUUUAUAUCU|CUUUAUAUCU|CAUUUCAGC|AUCCUCGUCU|3480
|3481|AUCUUUAAGU|UCUUAGUGCU|CUUUAUAUAU|UUUAUAUAUU|UCUCAUUUCU|AGGAUAAAGU|3540
|3541|UUUGAAAAU|CUAAUAACU|CGACAUCUUG|UUAUAGUAUA|UUUCAUUAU|AAAAUUAGGU|3600
|3601|AAUUAUAU|CAUAGGUUGA|CAUAGUUG|AAUUUCAGU|CAAUUGUUGA|AACGUCUGAA|3660
|3661|UCUCAGGAAAG|CUGAUGCUUU|CUCAACAGU|CUCAAACGUU|AUAUCAUCC|UUUACUCUUU|3720
|3721|UCUUCCAGAG|UCUAUAACU|UCCUCUUUC|AUACUUUUC|CAAUUGUAG|AUAUCAUCUU|3780
|3781|CGGAAGAAG|AGACACUAUC|UUUUACUAUC|UCUAAACUU|UCUAAACUU|UUUGUUCAA|3840|

FIG.6C-2

| | | | | | | |
|---|---|---|---|---|---|---|
| 3841 | AUCACAUGU | AAUAGAUGAU | UUGAUCAUUU | GAUGAUGGAC | CUAAUAUAGA | CAACGGCUCU | 3900 |
| 3901 | AUAGGAGAGG | UCAACCAGCC | CCCAUGUUU | GUGGGAAUCU | CGUUUGACUU | UAAACUUACU | 3960 |
| 3961 | CCAAGCUUGU | UAAAAAUUCU | AAUACUAUCA | UUCACUUCAC | CAGGAAGCAU | UGAAUAGAUG | 4020 |
| 4021 | CUUAACGCUU | GUACCUGCAC | AGCCCAUUAA | GCAAAAGGUA | UAACUUCAUU | AGGACAGCCU | 4080 |
| 4081 | UUCUCAGAA | GCAUUGUAAC | AUGUAUACUG | AGUACAUUA | GAUCAUCAAA | UAACUAUAU | 4140 |
| 4141 | GCGAAGAUUC | UGUGCAACAG | UUUGCUAAAU | GCCUGCAAUA | GAGAGAAUA | AUCGCUCCAU | 4200 |
| 4201 | UUACUAAAUC | UUUCAGAUAU | AAACUAUCUG | UCUGAUGAAG | AAGCAUAACU | CUUUUUGGG | 4260 |
| 4261 | UUCAAAGUUA | UGCAAAAAUC | UUUGAAAUGA | GCUUCAAUGC | UUCUAAACAA | CAUUCUGGC | 4320 |
| 4321 | AGAGAUGAGC | UUGAAAAGUC | UGUCAGCAUU | UUAUCAACCU | CUCCACUGGC | UAUUAAUGAU | 4380 |
| 4381 | GUUGCAUUAU | CAUCAGAGUG | CACAAUCCAU | CUAGUUUGGA | AAUCACAGUU | UUUGUAACAU | 4440 |
| 4441 | UCCAAAGUGU | UGUGAUAAGC | UUUCAUUGCA | CAAGAGUGAU | AAACAGAAGA | CAGAUAAUUU | 4500 |
| 4501 | AAAUGCCUU | GCAACCAAUU | CAUGCUAACA | GGGUAUGUGU | UUGCUGUCAA | GCCUUUGGUC | 4560 |
| 4561 | AAAGUCCUA | UGGCAGUUUC | AUUUUCCCCA | AAAGUUUGUU | GAGCUUUUCU | UAGAUCAAA | 4620 |
| 4621 | AAAAUAUCUG | UUGGUAUACA | AACCUCUUC | AAUUAAACAU | ACAUUAAGAU | GCAAUCUAUC | 4680 |
| 4681 | AUUAAGCUAG | CUUCACCAGU | AGUAAAAUU | GGAUUUAUA | UGAUAGCUAA | ACAUAUUUA | 4740 |
| 4741 | UAGGUGGUAA | GGCCUGAGC | CGACCAUUUC | GACUGAUCUG | CAGAUAGGAA | AGCCAAUCUU | 4800 |
| 4801 | GACUUCUUUG | AAUUUUGUU | UAAAAUAUCA | UUGUAAGACG | CAGAUAAUGU | CAAAGAUAAC | 4860 |
| 4861 | GUAGAAAGUG | CUCUUAUUU | AUGUCUCCA | CUUAUAGAUA | UGGCUUCCGA | UGGAUCACUC | 4920 |
| 4921 | UGCGCUACAU | GUUUGAAAUU | AUGCUCUAUA | AAAUAAAGCA | UCAUUUCAC | UUUCAAGCUC | 4980 |
| 4981 | AUCAAGUAUA | UUUCUCUGUC | UGUUUUGGUU | CUCUGCAUUU | UUUCAAAAAC | AGAAACUAGA | 5040 |
| 5041 | AAAUCUACAG | ACCCGGUGAC | AUUUUUAGCC | UGGACAUGA | CAAAUCAAG | CAUCUGCAAG | 5100 |
| 5101 | AAUGUGAGUU | UUUCCCUUC | UGUACCUUC | CCGAGGUUCA | UAACAGAAUC | UAGGUCUAUU | 5160 |
| 5161 | UCCAUCAUGU | CAUGGAACUG | UUUUACAAGG | UCAUAGAGCU | CCUCUACGAC | UUUUUAGAC | 5220 |
| 5221 | UUUAAAACUG | UACAUUAUAU | UCUAUUAUAU | AGUUUUGUUU | AGUUUAAUGU | UUCUACUGUU | 5280 |
| 5281 | AAGGAUGAU | UGUUUCUUAU | GAAUUUAGAU | GUUACAGAUU | UGAUUGAGAU | UAUUGAUCCA | 5340 |
| 5341 | CUACUAAUUA | UCUCUUUAAG | CUUUUCUAUA | UUUCUCCCA | AGAAUAAAUG | UCCCUACAGU | 5400 |
| 5401 | AAAAUCCA | CCAAUCUAUU | AUUUCUAUAU | AUUUUCUAUA | AAUGACACA | UUAUAAGCCC | 5460 |
| 5461 | GCUAGGUAUU | UCCUUCCA | AUUUCUAUA | AAGUUUGAU | UAUGAGGUC | UGCAUCCUG | 5520 |
| 5521 | AUAUCUCAU | CAGUACUUAU | UACAUUUCC | UAGGAAACU | UCUGAGCAUU | UUUUAGAC | 5580 |
| 5581 | GAUAUUUAU | AACAAGGGCU | CAGUACUUU | UAGGAUACU | UGUGACACU | UUUAAGUA | 5640 |
| 5641 | CCAACAUUUU | CUAUAUAUU | UCUAUAUCC | AGUUUGGCAU | UCUUAUCUGA | AAGCACUCU | 5700 |
| 5701 | UUUAUGGAGA | AUAGGUCUU | GUCAUCAAAC | AUGCUCUUCU | UAGGCAUAUU | UAGGGAUAU | 5760 |

FIG.6C-3

| | | | | |
|---|---|---|---|---|
| 5761 | AUGUUGAAAC | CUAAUUCUUU | UCUGAACUUU | AGCUCCCACU | CAGCAGGGAG | AUUUAAUAAG | 5820 |
| 5821 | CUUGUUAGAU | UGUGAACAUG | AUGUGCAGU | GAUUUAAGGCA | UCAUAUAAAU | AGCCAAAUAA | 5880 |
| 5881 | ACAUUAUUGU | ACAGGUCCUC | AAGUGUCAGU | AGAGUUGAUC | CUGUUAUAGG | ACAUUUUAUA | 5940 |
| 5941 | UUCAAGUUUG | UUAUCCCUCC | UAUAAUAUCA | UUUUCGUGGU | CCAACAAC | AGGCUUGGCA | 6000 |
| 6001 | UUUGUGCUUA | AAUUGAGAUC | UUCCAUUCUG | AACAAUAGUU | UUUUGAUUCC | AUUACGAAAU | 6060 |
| 6061 | AGAAUCUGC | CACAGUUAGU | UAUAUCAGGA | UCAGAUUUGU | CUCUAAGUA | UUCUUUUAUG | 6120 |
| 6121 | UUAGAAUAAU | CGGAUAGUCG | CAAAAAACCU | GCAUACCGCA | UGAAAUCAAA | AAUUCCCAUU | 6180 |
| 6181 | CUACUGAGCU | UUGUCACAGU | UCCUAUCAUG | ACAGAUGAAA | ACACAAUAUU | UAUUAAUAUC | 6240 |
| 6241 | UGUUUACAG | UCAUUGUCAU | AGAAAAGAGA | UUUACUUUUU | CUAUAUCUUU | AUUUUCAGC | 6300 |
| 6301 | GAUUUUCCGA | UUUCAUUAGC | UUUCUUUGAA | AAUGUGGAA | AACAUACAGG | AACUUUACUA | 6360 |
| 6361 | GGCGUUUUGA | AAAGCCUCAG | CAGCCUCACC | UGGUUUAGUC | UCUGCGGCCU | CAUUAUAUA | 6420 |
| 6421 | AUGAAAUAC | UACCACUUCG | GAAAUAGCUA | UAAAUUCUU | UAGUAUAACA | UAUGUAAAA | 6480 |
| 6481 | UGAUCUGACA | UGCUUCAUC | CACUAUAUGC | AAUGCUAUGU | AAGGAACUCC | CGAUCUCCG | 6540 |
| 6541 | GUGUUCAUUC | CAUCCCCUUU | GAAUGCUAAU | AGCAUCAUGC | UAGUAUUUGC | UGUGGUUAAU | 6600 |
| 6601 | AUCUUGAAAC | UUUCUUUAGU | CAGUACCUG | UCAGCCACCA | UUAAACCUUU | GGAGAAUGC | 6660 |
| 6661 | AUCAUGUCUU | CAGAGUAAUG | GUAAAUGGCU | AGAUCAUUG | AUAAUUUGUU | UAUCUUUUG | 6720 |
| 6721 | CAAGUCUCUA | AUUCAGUCUU | CAGUACUGAA | UCUUGAAUGU | ACAAGCAUC | AGGAUUUUUA | 6780 |
| 6781 | GCAUAUAUAU | UGAAAACAGA | UGUGAUCUUA | CCAUCCUCUA | UUAUAUAAA | AUAUGAAGU | 6840 |
| 6841 | AGAAAAAAAG | AGCCCUUAAA | UUUCUUUACC | CUAUAGCUAU | CAUCAUGUC | AUGCCUUAUC | 6900 |
| 6901 | AGUUUUUCA | UAUGAGUCAG | AGAAGACAG | UCUUGACAUG | AGUAAUCAUG | AUUGGGGUCA | 6960 |
| 6961 | GCCUGCCUUU | CAGAGGUACA | AUAUUCCAAG | CCUUUAGGAA | UCCUUUCUUU | UAUUUCUUCU | 7020 |
| 7021 | UUUUUAGAA | UUCUUUUCUU | AGAACUCAU | GCCUGUAUCU | CCUAUAUUCA | GCCUUUAAAA | 7080 |
| 7081 | UAGGUAGUUU | UGUUCUCCCA | CCAUUCUUAU | GCCUGUAUCU | AUCAUUUU | GUUUCUGGUU | 7140 |
| 7141 | AAACACGAAC | CUUGCUAUU | AUCUACAGU | CCAUUCUUUA | UUCUCUCAAC | UUUGAUACUC | 7200 |
| 7201 | CCGGUUUUA | UACUAUUC | AUCUUCAAGU | UCCUGCUUU | GACUUGU | UGUAUCACAA | 7260 |
| 7261 | CUUAGCUCUG | CUAACACAG | CUAAUAUGG | UUUGUUAUAU | CUCUGCUUU | AUUUGUUUGG | 7320 |
| 7321 | UAUUUGGC | UACUAUAUGG | GCUAUUAUAA | AUACCCUUG | AAGAACUUUU | GAAGCUCCC | 7380 |
| 7381 | CGAAACUUGU | UAAUAAUGC | GUUGUUGUAA | UCUACCUCUG | AGCACCAUUC | UAUCUUCAAA | 7440 |
| 7441 | CUGGGGACCA | AGCAUGGAA | AGUUAGUUUU | AGCAUCAGA | GAUCAGAGA | ACAGUAGGA | 7500 |
| 7501 | UACCUUUCU | CAUAUCAGC | AGCAUUCUGG | UUAAAAGCUG | UGGUAUGUC | AGGUAUCUCU | 7560 |
| 7561 | UUUCUUUC | UCUAAUUCUU | UCUAAUUCUA | AGCAUGAUCU | UCUCAAGGUG | UUUCCAUAC | 7620 |
| 7621 | AGAGAUUCCC | AUAUUUGCUG | CUUUUGGAU | AAGUGGUCUU | UCAAAUCAGC | UAAAUCAGCU | 7680 |

FIG.6C-4

| | | | | | |
|---|---|---|---|---|---|
| 7681 | UUGGCUCUA | UUUUAAAUU | GAUACAAGAG | UUUUGGUACC | CUUUAAAUUU | GUCAGCUAUA | 7740 |
| 7741 | UGCUGGUCAU | UCAUGUUUC | AAUGGGAAA | CAGAAAUUUC | CAAACAAAAA | AUGUAGUAUU | 7800 |
| 7801 | UCCUCUCUAG | GGAUUCAUC | UGUAACAAGU | GAAUCAAUUA | UUCUUUCAAU | AUCUUCGGAA | 7860 |
| 7861 | UAGGCUAUCU | CAGUAGGAUU | UCUUUCUUUG | UAUUUGCUGG | UCCAGUGACU | GAAAACACA | 7920 |
| 7921 | UCUUUAGAUC | CAAAAUCAUC | ACCUAAGAUU | CCCUGACUU | CAGAUUUGAU | UCUUUGAGUG | 7980 |
| 7981 | UUUGCAUAAU | AGUUCUCAC | CACUGUGGGU | GUGGUUCCAA | CUAUUUGCCC | AACAUAAGAA | 8040 |
| 8041 | AUAUUUAGCA | AUUUGGCAUU | UUUAUUCUUU | CUAGUAACAG | CUCCGUGCAA | UGCUGAUGGA | 8100 |
| 8101 | GAAUCUUCGA | AUUUCCCAA | AACCUGCUA | CUAGUAACAG | UGAUUGGCAU | CCCAGCAAUA | 8160 |
| 8161 | GGUUUCAAUA | UAACUAUAGA | AACGAAAACA | GGAUGCUCUU | CCAGGAAUGG | CUUUCCAUUC | 8220 |
| 8221 | ACUUUAUAU | CUUUGAAAGA | UUUCCAAAUA | UAUUUGUAGG | UAUUUCUCCA | UUGUUGGUU | 8280 |
| 8281 | UCAGCCUGG | CAUCGACAGA | UAUUUUCCAA | UCAUAAAAUGA | UUAAACAAAG | CUCACUGUUU | 8340 |
| 8341 | UUUGAUUCUU | UAUAUCUCAC | AUAGUUAUCA | GGGGGGCAU | UAGUUAAUGC | AUAUUCUUUA | 8400 |
| 8401 | UUUAUUCUCU | CAAACUCUAG | AUCAGAGAGC | UUGUAAUGC | AGGACUUUUU | GUUGAGUUCA | 8460 |
| 8461 | UCCAGAUAUU | CUCUUAGUGC | AUGCUCUAUC | UCCACUUCAU | UUCUUUGUUU | GGGCUUUAUU | 8520 |
| 8521 | CUCAGGUGCC | UGGAGAUCAG | AUGCAGCAG | CUCCCAAAA | AUGUCAGCC | UGUUUCUAGG | 8580 |
| 8581 | UAUUUUGCU | CAAACAGAGA | GACCAUCUCA | CUUAGCUUUU | UGCUAACAC | AGUGCCAUC | 8640 |
| 8641 | CCUUUGUUUA | GUCCUUCACC | AUCAGCAGUG | AUUUGACAA | UGACAUCCAC | CAUGUCUCA | 8700 |
| 8701 | UAAUUUUUG | CAUUAUUAUU | UAUAAUCACA | AUUUGACAA | UUAACUCUCU | AUUCUCUUA | 8760 |
| 8761 | UGUAAAUCCA | AAGCUAGAUC | GUGUUAGAA | UCUUCUGGGA | CCUCAAUAGA | CAACAGUAAA | 8820 |
| 8821 | GGGUUCCAU | UUUCUAUUAA | UUUUGUAUU | CCUACACAAU | UCUGGAAUGU | CAUGUUUGC | 8880 |
| 8881 | UGUUAUUGUA | UUGCUCU | | | | | 8897 |

| Fig. 15A |
| Fig. 15B |
| Fig. 15C |

| Fig.16A | Fig.16C |
|---------|---------|
| Fig.16B | Fig.16D |

NUCLEIC ACIDS ENCODING TOSPOVIRUS GENOME AND EXPRESSION THEREOF

This is a continuation of application Ser. No. 08/280,903, filed Jul. 27, 1994, now abandoned, which is a continuation of application Ser. No. 8/143,397, filed Oct. 26, 1993, now abandoned, which is a continuation of application Ser. No. 08/047,346, filed on Apr. 14, 1993, now abandoned, which is a continuation of application 07/694,734, filed May. 2, 1991, now abandoned, which is a continuation-in-part of application Ser. No. 07/446,024, filed Dec. 5, 1989, now abandoned, which is a continuation-in-part of application Ser. No. 07/431,259, filed Nov. 3, 1989, now abandoned.

The present invention related to plants having reduced susceptibility to infection with tospoviruses, genetic material used to generate this tolerance, probes for the isolation or diagnosis and processes for obtaining such plants and genetic material and probes.

INTRODUCTION

In general, virus infections have a variety of detrimental effects on e.g. growth, morphology and yield of plants. Also, virus infections often result in higher susceptibility of infected plants to other plant pathogens and plant pests. Transmission of plant viruses occurs generally by insect or fungal vectors or mechanically.

Plant breeders are trying continuously to develop varieties of crop plant species tolerant to or resistant to specific virus strains. Traditionally virus resistance genes are transferred from wild relatives into the commercial varieties by breeding. The transfer of an existing resistance from the gene pool of wild relatives to a cultivar is a tedious processing which the resistance gene(s) first have to be identified in a source (donor) plant species and resistance genes have to be combined with the perfect gene pool of a commercial variety. Resistance or tolerances generated in this way are in many cases only active against one or a few strains of the virus in question. Also, breeding cultivars for resistance to a particular virus species is often limited by a lack of genetic sources for this resistance within the crop species. Other approaches to prevent or decrease the effect of virus disease on plants are the use of chemicals or other methods which act against the virus vectors such as e.g. the use of insecticides, fungicides or good phytosanitary working conditions. However, the use of chemicals to combat virus disease by killing the vector is subject to increasing stricter regulations for use imposed by governments, confronting the growers with a decreasing scala of allowed chemical plant-protectants.

Alternately, a system called "cross-protection" can be employed. Cross-protection is a phenomenon in which infection of a plant with one strain of a virus protects the plant against superinfection with a second related virus strain. Thus, this latter method preferentially involves use of avirulent virus strains to infect plants, to inhibit a secondary infection with avirulent strain of the same virus. However, the use of this natural cross-protection system has several disadvantages. The method is very laborious because it requires inoculation of every planted crop, and carries the risk that due to a mutation the former avirulent strain becomes a more virulent strain, thereby creating a disease by itself. It is also possible that an avirulent virus strain on one plant species acts as avirulent strain on another plant species.

Several studies indicated that the viral coat protein of the protecting virus plays an important role in the cross-protection and that protection occurs when the resident virus and the challenging virus have the same or a closely related coat protein structures.

With the recent development of genetic manipulation and plant transformation systems new methods to create virus resistance have emerged. Genetically engineered cross-protection is a form of virus resistance which phenotypically resembles the natural cross-protection, but is achieved through expression of the genetic information of the viral coat protein from the genome of a genetically manipulated plant. The first successful experiments generating virus resistance by genetic engineering were performed by Beachy et al. (1985) and Abel et al. (1986). They showed that expression of the tobacco mosaic virus strain U1 (TMV-U1) coat protein gene from the genome of a transgenic plant resulted in a delay of symptom development after infection with any TMV strain. Similar results with respect to coat protein-mediated protection have been obtained for alfalfa mosaic virus (AMV), potato virus X (PVX) and cucumber mosaic virus (CMV).

Although TMV, CMV, AMV and PVX belong to different virus groups, they share a common architecture: in all these virions the viral RNA is a positive strand RNA encapsidated by a viral coat consisting of many individual but identical viral coat proteins.

Tospoviruses are essentially different from these plant virions. The genus of tospoviruses belongs to the Bunyaviridae. All tospoviruses are thrips transmitted. The virus particles are spherically shape (80–120 nm in diameter) and contain internal nucleocapsids surrounded by a lipid envelope studded with glycoprotein surface projections. The multipartite genome consists of linear single stranded RNA molecules of negative or ambisense polarity. The terminal nucleotides of these RNA molecules are characterised by a consensus sequence as follows: 5' AGAGCAAUX . . . GAUUGCUCU 3', wherein X is C or U. Typical members of the tospoviruses are tomato spotted wilt virus (TSWV) and Impatiens necrotic spot virus, also known as TSWV I-type.

The TSWV virion contains 4 distinct structural proteins: an internal nucleocapsid protein N of 29 kd and two membrane glycoproteins: $G_1$ of approximately 78 kd and $G_2$ of approximately 58 kd. In addition, minor amounts of a large protein L of approximately 260 kd have been detected in virus particles. The genome of TSWV consists of three linear single stranded RNA molecules of ±2900 nt (S RNA), ±5000 nt (M RNA) and ±8900 nt (L RNA), each tightly associated with nucleocapsid proteins and a few copies of the L protein to form circular nucleocapsids. A schematic structure outlining most properties of the TSWV virion is given in FIG. 1. Based on these and other properties TSWV has been classified as a representative of the tospoviruses group. Moreover, TSWV is considered as the typemember of the tospoviruses. Only circumstantial evidence was presented that suggested that a M RNA encoded gene is directly or indirectly involved in the synthesis of the $G_1$ membrane glycoprotein (Verkleij and Peters, 1983). The coding properties of the other RNA molecules and the polarity of the genomic RNA were still unknown prior to this invention.

As stated earlier, tospoviruses such as TSWV are transmitted by certain thrips species. The vector of TSWV belong to the family of Tripidae and include tobacco thrips (*Frankliniella fusca* (Hinds.)), western flower thrips (*F. occidentalis* (Pergande)), common blossom thrips (*F. Schultzei* (Trybom)), chilli thrips (*Scirtothrips dorsalis* (Hood)), *Thrips setosus* (Moulton), onion thrips (*T. tabaci* (Lindeman)), *F. intonsa* and *T. palmi*. Virus is acquired by the thrips only during their larval stages. Larvae can transmit the virus before they pupate but adults more commonly transmit the virus. Adults can remain infective throughout their life span.

The current distribution of TSWV covering all the continents makes it one of the most widely distributed plant viruses. The virus is widespread in temperate, subtropical and tropical climate zones throughout the world. At least 370 plant species representing 50 plant families, both mono- and dicotyledons, are naturally infected. The TSWV seriously affects the production of food and ornamental crops. Infections of plants with TSWV strains result generally in e.g. stunting, ringspots, dark purple-brown sunken spots, stem browning, flower breaking, necrotic and pigmental lesions and patterns, yellows and non-necrotic mottle, mosaic in greens or even total plant death. Most hosts only exhibit a part of these symptoms. The wide range of symptoms produced by TSWV has complicated the diagnosis and led to individual diseases being given several different names. Also, TSWV symptoms within the same plant species may vary depending on the age of the plant, time of infection during the life-cycle of the plant, nutritional levels and environmental conditions, especially temperature.

Although TSWV has been known for many years, is widely distributed, and causes economically important diseases in crops and ornamentals, limited progress has been made to identify sources for TSWV resistance genes. A multigenic TSWV tolerance has been identified in *Lycopersicon peruvianum*, but this resistance has not been transferred yet to cultivated tomatoes nor has a resistance source been identified for other crop species. The use of natural cross-protection systems to decrease the damage by severe TSWV strains is not well documented. Limited positive results have been reported for tomato and lettuce.

Therefore, the introduction of genetic information conferring resistance to tospovirus infection into plant gene pools by means of genetic manipulation provides breeder and grower a new method to combat tospoviral diseases.

DETAILED DESCRIPTION

The present invention provides recombinant DNA constructs comprising a DNA sequence coding for transcription into a) an RNA sequence of tospoviruses or an RNA sequence homologous thereto;

b) an RNA sequence according to a) encoding for a tospovirus protein in which one or more codons have been replaced by their synonyms (i.e. codons corresponding to the same amino acid or termination signal), or a part thereof; or an RNA sequence homologous thereto, or c) an RNA sequence complementary to an RNA sequence according to a) or b), which DNA is under expression control of a promoter functioning in plants and has a terminator functional in plants.

The DNA sequences defined under a), b) and c) hereinabove, are, hereinafter, for convenience referred to as a "TSWV Related DNA Sequences". A TSWV Related DNA Sequence according to the invention may be modified, if desired, to create mutants or modified sequences homologous to a TSWV Related DNA Sequence from which they are derived using methods known to those skilled in the art such as site-directed mutagenesis. Such mutants or modified coding sequences are therefore within the spirit and the scope of this invention.

The term RNA sequence of a tospovirus refers to a sequence of the S, M or L RNA strand, in particular of the S or L RNA strand, preferable of the S RNA strand of a tospovirus.

The term RNA sequence homologous to an RNA sequence of a tospovirus refers to a RNA sequence of a tospovirus wherein a number of nucleotides have been deleted and/or added but is still capable of hybridization to a nucleotide sequence complementary to an RNA sequence of a tospovirus under appropriate hybridization conditions. For the purpose of the invention appropriate hybridization conditions conveniently include an incubation for 16 hours at 42° C., in a buffer system comprising 5 x standard saline citrate (SSC), 0.5% sodium dodecylsulphate (SDS), 5 x Denhardt's solution, 50% formamide and 100 μg/ml carrier DNA (hereinafter the buffer system), followed by washing 3 times with a buffer comprising 1 x SSC and 0.1% SDS at 65° C. for approximately one hour each time.

Preferred hybridization conditions for the purpose of the invention involve incubation in the buffer system for 16 hours at 49° C. and washing 3 times with a buffer comprising 0.1 x SSC and 0.1% SDS at 55° C. for approximately one hour each time. Most preferred hybridization conditions for the purpose of the invention involve incubation in the buffer system for 16 hours at 55° C. and washing 3 times with a buffer 0.1 x SSC and 0.1% SDS at 65° C. for approximately one hour each time.

The length of the TSWV Related DNA Sequence will i.a. depend on the particular strategy to be followed, as will become apparent from the description hereinafter. In general, it will be desirable that the TSWV Related DNA Sequence comprises at least 20, suitably 50 or more nucleotides.

The term promoter as used herein refers to the nucleotide sequence upstream from the transcriptional start site and containing all the regulatory regions required for transcription including the region coding for the leader sequence of mRNA (which leader sequence comprises the ribosomal binding site and initiates translation at the AUG start codon).

Examples or promoters suitable for use in DNA constructs of the invention include viral, fungal, bacterial, animal and plant derived promoters functioning in plant cells. The promoter may express the DNA constitutively or differentially. Suitable examples of promoters differentially regulating DNA expression are promoters inducible by disease vectors, such as thrips, e.g. so-called wound inducible promoters. It will be appreciated that the promoter employed should give rise to the expression of a TSWV Related DNA Sequence at a rate sufficient to produce the amount of RNA necessary to decrease the tospovirus susceptibility of the transformed plant. The necessary amount of RNA to be transcribed may vary with the type of plant involved. Particularly preferred promoters include the cauliflower mosaic virus 35S (CaMV 35S) promoter, derivatives thereof, and a promoter inducible after wounding by a disease vector such as thrips, e.g. a wound inducible promoter.

The term terminator as used herein refers to a DNA sequence at the end of a transcriptional unit that signals termination of transcription. Terminators are DNA 3'-non-translated sequences that contain a polyadenylation signal, that causes the addition of polyadenylate sequences to the 3'-end of the primary transcript. Terminators active in plant cells are known and described in the literature. They may be isolated from for example bacteria, fungi, viruses, animal and plants. Examples of terminators particularly suitable for use in the DNA constructs of the invention include the nopaline synthase terminator of *A. tumefaciens*, the 35S terminator of CaMV and the zein termination from *Zea mays*.

According to the terminology employed in the present specification, an RNA sequence is complementary to another RNA sequence if it is able to form a hydrogen-bonded complex with it, according to rules of base pairing under appropriate hybridization conditions (as defined hereinabove).

The invention also provides a vector capable of introducing the DNA construct of the invention into plants and methods of producing such vectors.

The term vector employed herein refer to a vehicle by means of which DNA fragments can be incorporated in a host organism.

The term plants is used herein in a wide sense and refers to differentiated plants as well as undifferentiated plant material such as protoplasts, plant cells, seeds, plantlets etc. that under appropriate conditions can develop into mature plants, the progeny thereof and parts thereof as cuttings and fruits of such plants.

The invention further provides plants comprising in their genome a DNA construct of the invention, and methods of producing such plants.

The plants according to the invention have reduced susceptibility to disease induced by tospoviruses and do not have the disadvantages and limitations of plants obtained by the classical methods as discussed hereinabove.

Examples of plants susceptible to tospoviruses such as TSWV include but are not limited to Ageratum, alfalfa, Amaranthus, Anthirthinum, Aquilegia, aubergine, beet, Begonia, broad bean, broccoli, brussels sprouts, cabbage, cauliflower, celery, chicory, Chrysanthemum, Cineraria, clover, Cosmos, cowpea, cucumber, cyclamen, Dahlia, Datura, Delphinium, endive, Gerbera, Gladiolus, Gloxinia, gourd, groundnut, Hippeastrun, Impatiens, lettuce, melon, Mesembryanthemum, onion, papaya, pea, peanut, pepper, petunia, pineapple, potato, Primula, Saint Paulia, safflower, Salpiglossis, snap bean, soybean, spinach, squash, sugarbeet, sunflower, Tagetes, tobacco, tomato, Verbena, Vinca, watermelon, Zinnia. The invention relates in particular to these listed plants comprising in their plant genome a DNA construct of the invention.

Since TSWV is the typemember of the tospoviruses, the particular features of tospoviruses are hereinafter illustrated employing TSWV as an example.

The S, M and L RNA are single stranded RNA molecules. The S RNA is approximately 2,900 nucleotides long and comprises two genes, one encoding a non-structural protein (NSs) in viral sense, the other one encoding the nucleocapsid protein (N) in viral complementary sense. The intergenic region between the NSs- and N-gene can be folded into a hairpin structure. The 5=- and 3'-terminal sequences of the S RNA are capable of hybridizing to each other such that the first nucleotide is opposite (and complementary) to the last nucleotide of said S RNA strand. We designate hereinafter the double-stranded structure obtained in hybridizing both RNA termini for convenience "pan-handle".

The M RNA strand has approximately 5000 nucleotides. It contains one long open reading frame in viral complementary sense. This open reading frame is translated on polysomes located on the endoplasmic reticulum where the nascent polypepride chain is cleaved co-translationally to form the spike proteins $G_1$ and $G_2$ respectively. Similar to the S RNA the termini of the M RNA strand are complementary to each other and may likewise hybridize to form a "pan-handle".

The L RNA strand has approximately 8900 nucleotides. It contains complementary 3'and 5'ends for a length of 62 to 66 nucleotides. The RNA is of negative polarity, with on large open reading frame (ORF) located as the viral complementary strand. This ORF corresponds with a primary translation product of 2875 amino acids in length with a predicted Mr of 331,500. Comparison with the polymerase proteins of other negative-strand viruses indicates that this protein most likely represents the viral polymerase. In some mutant strains shortened L RNA molecules have been found in addition to the wild type, full length L RNA. These shortened L RNAs however, do always possess the characteristic terminal nucleotide sequences and thus are capable of forming "pin-handle" structures. They are also encapsidated with nucleocapsid protein and included in virus particles. These presence suppresses symptom development resulting in less severe detrimental effects. Hence, these shortened L RNA molecules can be regarded as defective interfering (DI) RNAs, a term known to those skilled in the art.

A preferred embodiment of the invention relates to DNA constructs of the invention coding for transcription into tospovirus-RNA sequences of a "pan-handle", or into tospovirus-RNA sequences homologous thereto.

Another preferred embodiment of the invention relates to DNA constructs of the invention coding for transcription into tospovirus-RNA sequences of an open reading frame in viral complementary sense (i.e. having negative polarity), or into corresponding RNA sequences in which one or more codons have been replaced by their synonyms, or into RNA sequences homologous thereto.

A further preferred embodiment of the invention relates to DNA constructs of the invention coding for transcription into tospovirus-RNA sequence of a hairpin, or into RNA sequences homologous thereto.

Preferably the tospovirus-RNA sequence referred to hereinabove have at least 20, more preferably at least 50 nucleotides.

Examples of DNA constructs suitable for use according to the invention include TSWV Related DNA Sequences coding for transcription into (reference is made to FIG. 4 for S RNA nucleotide sequences, FIG. 6A for M RNA nucleotide sequences and FIG. 6B for L RNA nucleotide sequences, except that the sequences xxvii to xxx are shown in FIG. 6c)

i) the S RNA nucleotide sequence 1 to 2915;
ii) the S RNA nucleotide sequence 89 to 1483;
iii) the S RNA hairpin;
iv) the S RNA "pan-handle";
v) the S RNA nucleotide sequence 2763 to 1987;
vi) the L RNA nucleotide sequence 4462 to 1;
vii) the L RNA nucleotide sequence 41 to 2;
viii) the L RNA nucleotide sequence 3980 to 46;
ix) the L RNA nucleotide sequence (6706÷n) to (4462÷n); whereby n is the number of nucleotides of the gap between nucleotide 4462 (U) and the subsequent nucleotide (C) shown in FIG. 6B
x) the L RNA nucleotide sequence (6706÷n) to (6016÷n); wherein n is a defined hereinabove;
xi) the L RNA "pan-handle";
xii) an RNA sequence complementary to the S RNA nucleotide sequence 1987 to 2763;
xiii) an RNA sequence complementary to the S RNA nucleotide sequence 89 to 1483;
xiv) an RNA sequence complementary to the L RNA nucleotide sequence to 1 to 4462;
xv) an RNA sequence complementary to the L RNA nucleotide sequence 2 to 41;

xvi) an RNA sequence complementary to the L RNA nucleotide sequence 46 to 3980;

xvii) an RNA sequence complementary to the L RNA nucleotide sequence (4462÷n) to (6706÷n), wherein n is as defined above;

xviii) an RNA sequence complementary to the L RNA nucleotide sequence (6016÷n) to (6706÷n), wherein n is as defined above;

xix) S RNA nucleotide sequence 89 to 1483 in which one or more codons have been replaced by their synonyms;

xx) S RNA nucleotide sequence 2763 to 1987 in which one or more codons have been replaced by their synonyms;

xxi) L RNA nucleotide sequence 3980 to 236 in which one or more codons have been replaced by their synonyms;

xxii) L RNA nucleotide sequence 4462 to 236 in which one or more codons have been replaced by their synonyms;

xxiii) L RNA nucleotide sequence (6672÷n) to (4462÷n) in which one or more codons have been replaced by their synonyms;

xxiv) L RNA nucleotide sequence (6672÷n) to (6016÷n) in which one or more codons have been replaced by their synonyms;

xxv) the M RNA nucleotide sequence (m−574) to m, wherein m is the total number of nucleotides of the M RNA;

xxvi) an RNA sequence complementary to the M RNA nucleotide sequence (m−574) to m, wherein m is as defined hereinabove;

xxvii) the L RNA nucleotide sequence 8897 to 1 xxviii) the L RNA nucleotide sequence 6653 to 4463 xxix) an RNA sequence complementary to the L RNA nucleotide sequence 4463 to 6653 xxx) L RNA nucleotide sequence 6653 to 4463 in which one or more codons have been replaced by their synonyms.

xxxi) an RNA sequence complementary to the L RNA nucleotide sequence 34 to 8659 xxxii) L RNA sequence 8659 to 34 in which one or more codons have been replaced by their synonyms xxxiii) RNA sequences homologous to the nucleotide sequences defined under i) to xviii), xxv), xxvi) to xxix or xxxi hereinabove;

xxxiv) the M RNA nucleotide sequence from (m−26) to (m−574) in which one or more of the codons have been replaced by their synonyms.

xxxv) fragments of sequences defined under i) to xxxiv) hereinabove.

Preferred TSWV Related DNA Sequences code for transcription into the RNA sequences according to ii), iii), iv), v), viii), ix) or xi) as defined above, or into RNA sequences homologous thereto, or into fragments thereof comprising at least 20, more preferably at least 50 nucleotides.

According to another preferred embodiments of the invention the DNA constructs of the invention comprise TSWV Related DNA Sequences coding for transcription into a combination of the 5' and 3' terminal sequences of the viral S, M or L RNA respectively, more preferably of the S or L RNA, in particular of the S RNA.

The invention further provides probes to diagnose suspected plants for infection with tospovirus such as TSWV. Such probes comprise a labeled oligonucleotide (RNA or DNA) sequence complementary to an RNA sequence of tospoviruses such as TSWV (for the definition of the terms complementary see hereinabove). The desired length of the sequence and appropriate method for diagnostic use of probes are known by those skilled in the art. A suitable probe will conveniently comprise a sequence of a least 15 preferably more than 30, more preferably from about 400 to 600 nucleotides complementary to an RNA sequence to tospoviruses such as TSWV.

Probes according to the invention are useful, in that they allow a person skilled in the art to identify tospovirus RNA or parts thereof in infected plant material, e.g. for diagnostic purposes prior to full expression of the disease symptoms.

The invention accordingly also provides a diagnostic method of determining tospovirus infection in plants which comprises detecting tospovirus replicative forms employing the probes of the invention in dot-blot type assays.

Probes according to the invention are useful, in that they allow a person skilled in the art to construct and to use chimenic genes comprising a DNA sequence corresponding to an RNA sequence of tospovirus.

The DNA constructs of the invention may be obtained by insertion of the TSWV Related DNA Sequence in an appropriate expression vector, such that it is brought under expression control of a promoter functioning in plants and its transcription terminated by a terminator.

The term expression vector as used here to a vector containing a promoter and a terminator which function in plant cells.

The insertion of the TSWV Related DNA Sequence into an appropriate expression vector may be carried out in a manner known per se. Suitable procedures are also illustrated by the examples hereinafter.

Likewise the construction of appropriate expression vector may be carried out in a manner known per se.

The plants according to the invention may be obtained by a) inserting into the genome of a plant cell a DNA construct according to the invention;

b) obtaining transformed cells; and c) regenerating from the transformed cells genetically transformed plants.

The DNA vector of the invention may be inserted into the plant genome of plants susceptible to TSWV infection. Such plant transformation may be carried out employing techniques known per se for the transformation of plants, such as the plant transformation techniques involving the Ti plasmids derived from *Agrobacterium tumefaciens, A. rhizogenes* or modifications thereof, naked DNA transformation or electroporation of isolated plant cells or organized plant structures, the use of micro-projectiles to deliver DNA, the use of laser systems, liposomes, or viruses or pollen as transformation vectors and the like.

The plants of the invention may be monitored for expression of a TSWV Related DNA Sequence by methods known in the art, including Northern analysis, Southern analysis, PCR techniques and/or immunological techniques. The plants of the invention show decreased susceptibility to TSWV infection as demonstrated by tests whereby said plants are exposed to TSWV preferentially at a concentration in the range where the rate of disease symptoms correlates linearly with the TSWV concentration in the inoculum.

Methods suitable for TSWV inoculation are known in the art; they include mechanical inoculation and, in particular, the use of appropriate vectors.

The plants of the invention may of course also be obtained by crossing of a obtained plant according to the methods of the invention with another plant to produce plants having in their plant genonme a DNA construct of the invention.

The invention is illustrated by the following non-limitative examples and the attached Figures.

FIG. 1 gives an overview of the structure of the tomato spotted wilt virus.

FIG. 2 gives a review of the cloning strategy employed for TSWV S RNA.

FIG. 3 gives a review of the cloning strategy employed for TSWV L RNA.

FIG 4 shows the sequence and genomic organization of the TSWV S RNA. The amino acid sequence of the non-structural protein NSs (89 –1483) is outlined above, that of the nucleocapsid protein N (2763–1987) under the corresponding RNA nucleotide sequence.

FIG. 5 gives the distribution of translation and termination codons for all reading frames of the S RNA (FIG. 5A) and of the L RNA (FIG. 5B with a gap between nucleotides 4462 and 6653, FIG. 5C without said gap). Full bars indicate stop codons, half bars ATG start codons.

Figure 6B-2:
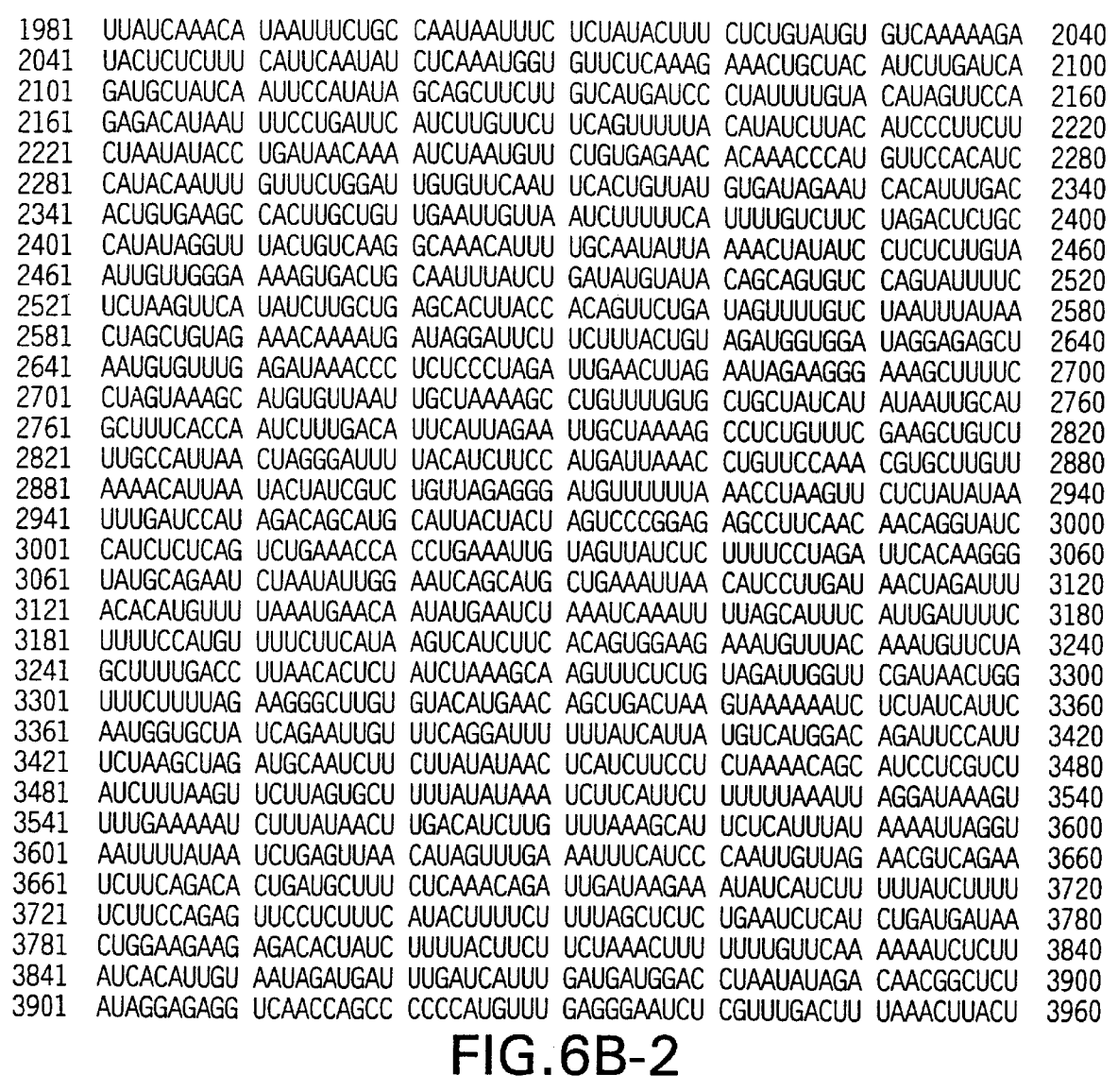

FIG. 6 shows the nucleotide sequence of the TSWV M RNA (FIG. 6A) and of L RNA (FIG. 6B shows part of the structure, FIG. 6C the complete structure.

FIG. 7 gives a schematic review of the construction of a suitable expression vector (pZU-A).

FIG. 8 gives a schematic review of the construction of a suitable expression vector (pZU-B).

FIG. 9 gives a schematic review of the construction of a suitable plasmid (pTSWV-N) comprising the nucleocapsid N protein gene.

FIG. 10 gives a schematic review of the construction of a suitable plasmid (pTSWV-NSs) comprising the nucleocapsid NSs-protein gene.

FIG. 11 gives a schematic example of the construction of a plant transformation vector pTSWV-NAB, a DNA construct according to the invention.

FIG. 12 gives a schematic example of the construction of a plant transformation vector pTSWV-Nmut BB, a DNA construct according to the invention.

FIG. 13 gives a schematic example of the construction of a plant transformation vector pTSWV-NSsAB, a DNA construct according to the invention.

FIG. 14 gives a schematic example of the construction of a plant transformation vector pTSWV-NSsmut BB, a DNA construct according to the invention.

FIG. 15 shows the "pan-handle" region of TSWV S RNA.

FIG. 16 shows the hairpin region of TSWV S RNA.

Figure 1:
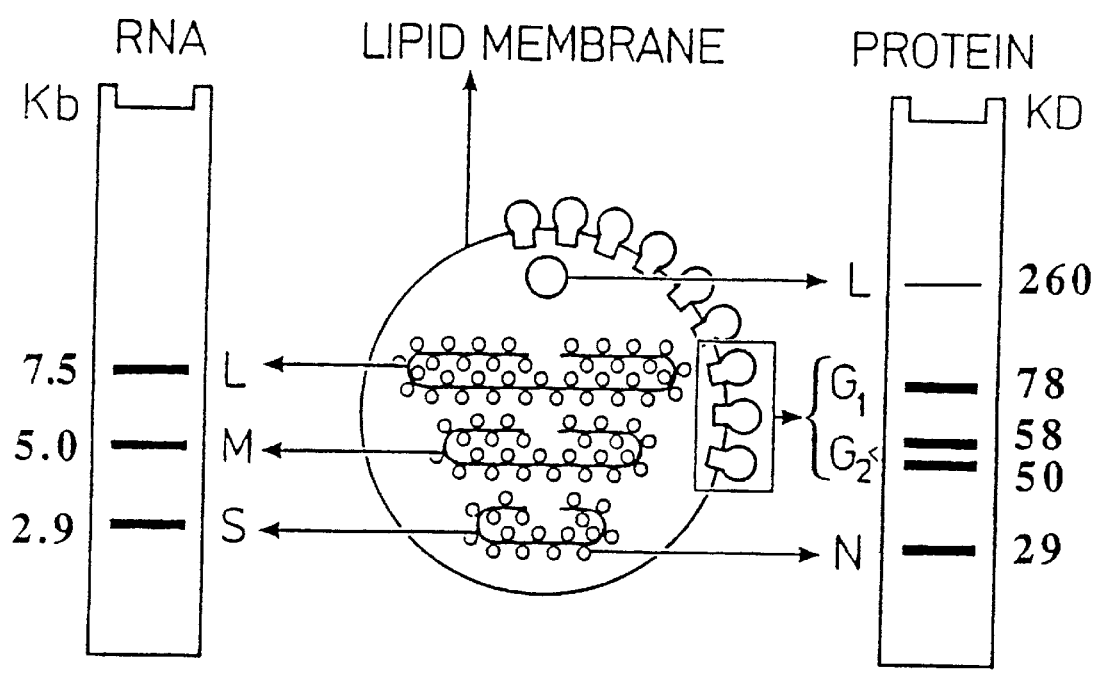

Suitable examples of preferred TSWV Related DNA Sequences coding for transcription into a sequence of the hairpin structure of S RNA or of RNA sequences homologous thereto are sequences coding for the 1583 –1708 nucleotide of S RNA, for the 1709–1835 nucleotide sequence of S RNA, for the 1583–1935 nucleotide sequence of the S RNA or for a sequence homologous to such sequences.

Suitable examples of preferred TSWV Related DNA Sequences coding for transcription into a sequence of the "pan-handle" region of S RNA or of RNA sequences homologous thereto is the combination of the sequences coding for the 1–170 and 2,850–2916 nucleotide sequence of S RNA, or for sequences homologous to such sequences.

Suitable examples of preferred TSWV Related DNA Sequences coding for transcription into a "pan-handle" region of L RNA or of RNA sequences homologous thereto is the combination of sequences coding for the first 80, in particular the first 65 nucleotides from the 5'-end of the viral L RNA and the last 80, in particular the last 65 nucleotides from the 3'-end of the viral L RNA, or for sequences homologous to such sequences or derivatives thereof.

Other objects, features, advantages of the present invention will become apparent from the following examples.

References are abbreviated to the first authors name, full references are listed later.

MATERIALS AND METHODS

All TSWV RNA derived sequences presented in here are depicted as DNA sequences for the sole purpose of uniformity only. A person skilled in the art appreciates that this is done for convenience only.

Cultivars of *Nicotiana tabacum* and *Petunia hybrida*, used in plant transformation studies, are grown under standard greenhouse conditions. Axenic explant material is grown on standard MS media (Murashige and Skood, 1962) containing appropriate phytohormones and sucrose concentrations.

*E. coli* bacteria are grown on rotary shakers at 37° C. in standard LB-medium. *Agrobacterium tumefaciens* strains are grown at 28° C. in MinA medium supplemented with 0.1% glucose (Ausubel et al., 1987).

In all cloning procedures the *E. coli* strain JM83, (F–, Δ(lac-pro), ara, rpsL, Ø80, dlacZM15) is used as a recipient for recombinant plasmids.

Binary vectors are conjugated to *Agrobacterium tumefaciens* strain LBA 4404, a strain containing the Ti-plasmid vir region, (Hoekema et al., 1983) in standard triparental matings using the *E. coli* HB101, containing the plasmid pRK2013 as a helper strain. (Figurski and Helinski, 1979). Appropriate *Agrobacterium tumefaciens* recipients are selected on media containing rifampicin (50 µg/ml) and kanamycine (50 µg/ml).

Cloning of fragments in the vector pUC19 (Yanish-Perron et al., 1985), pBluescript (Stratagene), pBIN 19 (Bevan et al., 1984) or derivatives, restriction enzyme analysis of DNA, transformation to *E. coli* recipient strains, isolation of plasmid DNA on small as well as large scale, nick-translation, in vitro transcription, DNA sequencing, Southern blotting and DNA gel electrophoresis are performed according to standard procedures (Maniatis et al., 1982; Ausubel et al., 1987).

EXAMPLES

Example 1

Isolation of TSWV particles and the genetic material therein

Tomato spotted wilt virus strain CPNHl, a Brazilian isolate from tomato, is maintained on tomato by grafting. Virus is purified from systemically infected *Nicotiana rustica* leaves, after mechanical inoculation essentially as described by Tas et al. (1977). It is essential to maintain all material used in this isolation procedure at 4° C. Twelve days after inoculation of 100 grams of infected leaves are harvested and ground 5–10 seconds at low speed setting in 5 volumes extraction buffer (0.1 M $NAH_2PO_4$, 0.01 M $NA_2SO_3$, pH 7) in a Waring blender. The suspension is filtered through cheesecloth and the filtrate is centrifuged for 10 minutes at 16,000×g. The resulting pellet is resuspended in three volumes resuspensionbuffer (0.01 M $NAH_2PO_4$, 0.01 M $Na_2SO_3$, pH 7). The pellet is dissolved by stirring carefully at 4° C. After centrifugation for 10 minutes at 12,500×g the pellet is discarded and the supernatant is centrifuged again for 20 minutes at 50,000×g. The pellet is resuspended in 0.2 volume of resuspensionbuffer (0.1 M $NAH_2PO_4$, 0.01 M $NA_2SO_3$, pH 7) and kept on ice for 30 minutes. Antiserum raised in rabbits against material from non-infected Nicotiana rustica is added to the solution, carefully stirred for 1 hour and non-viral complexes are pelleted by 10 minutes centrifugation at 16,00 x g. The cleared supernatant is loaded on a linear 5–40% sucrose gradient in resuspensionbuffer 0.1 M $NAH_2PO_4$, 0.01 M $NA_2SO_3$, pH 7, and spun for 45 minutes at 95,000 x g. The opalescent band containing TSWV virions is carefully collected with a syringe and diluted 4 times with resuspensionbuffer. Washed virions are pelleted by centrifugation for 1.5 hours at 21,000 x g and resuspended in one volume resuspensionbuffer. Generally, 100 grams of leaf material yields approximately 0.5 mg of TSWV virions. TSWV RNA is recovered preferentially from purified virus preparations by SDS-phenol extractions followed by ethanol precipitation. From 1 mg TSWV 1–5 µg of RNA is extracted. The intactness of the isolated RNA molecules is analysis by electrophoresis on an agarose gel. Three distinct RNA molecules are identified with apparent sizes of 2900 nucleotides (S RNA), 5000 nucleotides (M RNA) and 7500 nucleotides (L RNA) respectively.

Example 2

Sequence determination of the 3'-termini of the TWSV viral RNAs

For direct RNA sequencing TSWV RNA is extracted from purified nucleocapsids essentially according to Verkleij et al. (1983). Twelve days after inoculation 100 grams of infected leaves are harvested and ground 5–10 seconds at low speed setting in four volumes TAS-E buffer (0.01 M EDTA, 0.01 M $Na_2SO_3$. 0.1% cysteine, 0.1 M TRIS pH 8.0) in a Waring blender. The suspension is filtered through cheesecloth and centrifuged 10 minutes at 1,100×g. Nucleocapsids are recovered from this supernatant by 30 minutes centrifugation at 66,000×g. The pellet is carefully resuspended in one volume TAS-R buffer (1% Nonidet NP-40, 0.01 M EDTA, 0.01 M $Na_2SO_3$. 0.1% cysteine, 0.01 M glycine, 0.01 M TRIS pH 7.9). The pellet is dissolved by stirring carefully for 30 minutes at 4° C. The supernatant is cleared by a 10 minutes centrifugation at 16,000×g. Crude nucleocapsids are collected from the cleared supernatant by sedimentation through a 30% sucrose cushion for 1 hour at 105,000×g. The nucleocapsid pellet is resuspended in 400 µl 0.01 M Na-citrate pH 6.5, layered on a 20–40% sucrose (in 0.01 M Na-citrate pH 6.5) and spun for 2 hours at 280,000×g. The three different opalescent bands, respectively L, M and S nucleocapsid, are collected separately. TSWV RNA is recovered preferentially from purified nucleocapsid, preparations by SDS-phenol extractions followed by ethanol precipitation. Routinely 100 µg of RNA are obtained from 100 grams of infected leaves. The 3'-ends of the separate TSWV RNAs are labeled using RNA ligase and 5'-[$^{32}P$]pCp. These end-labeled RNA molecules are separated on a low gelling temperature agarose gel (Wieslander, 1979). The enzymatic approach described by Clerx-Van Haaster and Bishop (1980) and Clerx-Van Haaster et al. (1982) is used to determine the 30 terminal nucleotides of the 3'- and 5'-ends of both S and M RNA.

Synthetic oligonucleotides complementary to the 3'-termini are synthesized using a commercially available system (Applied Biosystems) and used for dideoxy-sequencing with reverse transcriptase.

Example 3 cDNA Cloning of TSWV Generic Material

Oligonucleotides complementary to the 3'-ends of the S and L RNA are used for priming first strand cDNA synthesis. With these primers, double stranded DNA to TSWV RNA is synthesized in principle according to Bubler and Hoffman (1983). Two different approaches are used to generate cDNA clones to the TSWV viral RNAs. A first series of clones is obtained by random priming of the TSWV RNA using fragmented single stranded calf thymus DNA, followed by first and second strand cDNA synthesis. cDNA is made blunt-ended using T4-DNA polymerase and ligated with T4 ligase into the SmaI site of pUC19. A second series of TSWV cDNA clones is obtained by priming first strand DNA synthesis with the oligonucleotides complementary to the 20 terminal nucleotides at the 3'-ends of the TSWV RNAs. After second strand synthesis, treatment with T4 DNA polymerase to create blunt ends, phosphorylated EcoRI linkers are ligated to the ends of the cDNAs essentially according to Huynh et al. (1985). After restriction of these cDNA molecules with EcoRI, the cDNA fragments are ligated in the EcoRI site of lambda gt10. cDNA clones from both series containing viral inserts are selected via colony hybridization, essentially according to Grunstein and Hogness (1975) using [$^{32}P$]-labeled, randomly primed first strand cDNA as a probe. Sets of overlapping cDNA clones are selected by Southern analysis followed by plasmid and/or phage walking, in order to construct restriction maps, based on cDNA derived sequences of the S (FIG. 2) and L RNA (FIG. 3).

Example 4

Sequence Determination of the TSWV S, M and L RNA

In order to determine the sequence of the S RNA 4 selected cDNA clones are subcloned in M13mp18, resulting in the plasmids pS614, pS608, pS520 and pS514, as described above (FIG. 2). These clones are sequenced in both directions using the standard protocol of Yanish-Perron et al. (1985). The nucleotide sequence of the 3'-end of the S RNA is determined by primer extension of the synthetic oligonucleotide S1 (5'd(GAGCAATCGTGTCAATTTTG)), which is complementary to the 20 nucleotides of the 3'-terminus. A second synthetic oligonucleotide S3 complementary to the nucleotides 30 to 50 from the 5'-end of the viral S RNA is used to verify the 5'-terminal sequence of the S RNA by primer extension. Sequence data from the TSWV SRNA (2916 nt) are summarized in FIG. 4.

Figure 5A:
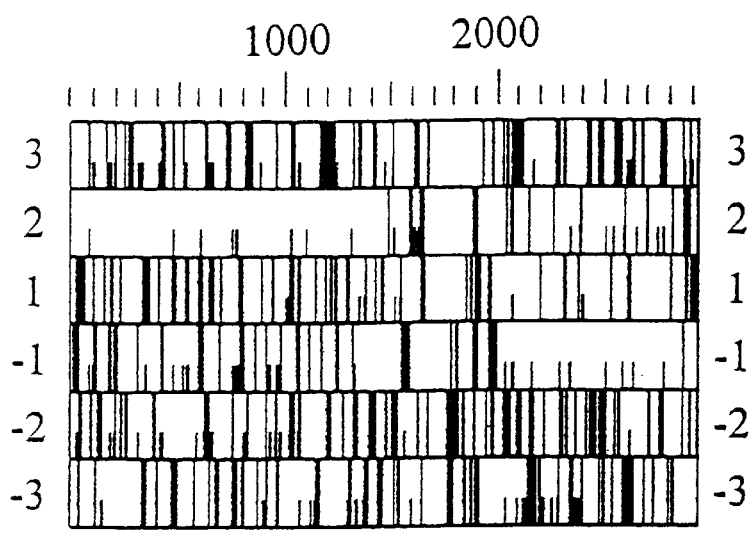

Computer simulated translation of the 6 different reading frames on the viral stand and viral complementary strand reveals the presence of two putative open reading frames (see FIG. 5A). On the viral strand an open reading frame is found starting at position 89 and terminating at an UAA stopcodon at position 1483 possibly encoding a protein of 464 amino acids with a molecular weight of 52.4 kd. This protein is most likely a non-structural protein, tentatively designated NSs. The other open reading frame is located on the viral complementary strand from position 2763 to 1987, encoding a 258 amino acids long polypeptide with a molecular weight of 28.8 kd. This open reading frame possibly encodes the viral nucleocapsid protein N.

To verify this assumption the amino acid composition of the purified nucleocapsid protein is determined and compared with the deduced composition from the sequence data. Also, the putative nucleocapsid encoding N protein gene is inserted into pBluescript. Using T7 RNA polymerase the N protein gene is transcribed in vitro. This in vitro synthesized transcript is subsequently translated in an in vitro rabbit reticulocyte lysate (New England Nuclear: NEN) system in the presence of [$^{35}S$] labeled methionine (NEN). A protein with a molecular weight identical to the native nucleocapsid protein could be precipitated from the synthesized radioactive proteins, when antibodies raised against purified nucleocapsid protein are used, following procedures essentially as described (Van Grinsven et al, 1986). This indicates that the N protein gene encodes the viral nucleocapsid protein. FIG. 5A shows the coding capacities of the viral and the viral complementary strand of the S RNA indicating the NSs and N protein gene respectively, both genes being expressed from subgenomic mRNAs. Thus, the unique situation occurs that a plant virus RNA has an ambisense gene arrangement. Other important features of this S RNA sequence is the existence of complementary terminal repeats capable of forming so-called "pan-handle" structures. These structures play an important role in replication and transcription of the viral RNA. Another putative regulatory element is the hairpin structure in the intergenic region of the S RNA, which most likely contains the transcription termination signals for both subgenomic mRNAs, encoding respectively the N and NSs-protein.

The nucleotide sequence of the TSWV M and L RNA was elucidated employing the same strategies and methods followed to determine the nucleotide sequence of the S RNA.

Example 5

Construction of an Expression Vector pZU-A

Figure 7:
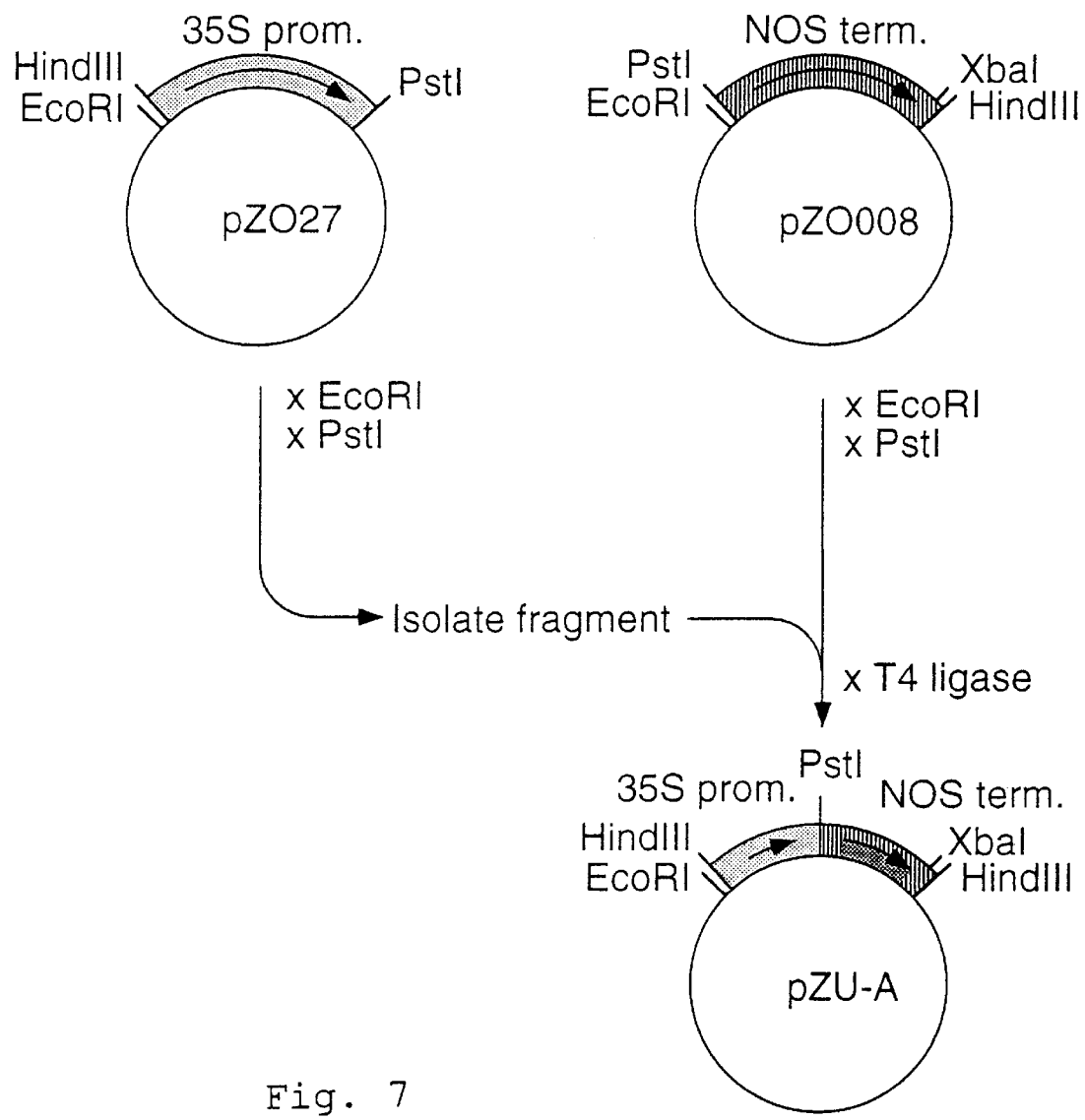

The 35S cauliflower mosaic virus (CaMV) promoter fragment is isolated from the recombinant plasmid pZO27, a derivative of pUC19 carrying as a 444 bp HindIII-PstI fragment the HincII-HphI region of the 35S promoter of CaMV strain Cabb-S (Franck et al., 1980). The nucleotide sequences of CaMV strains are very similar for the different strains. The 35S promoter fragment is excised from pZO27 as a 472 bp EcoRI-PstI fragment which contains: a part of the polylinker region, 437 bp of the non-transcribed region, the transcription initiation site and 7 bp of the non-translated leader region but not containing any 35S translational initiators. This 35S promoter fragment is ligated using T4 ligase into EcoRI-PstI linearized pZO008. This plasmid pZO008 carries the nopaline synthase (NOS) terminator as a 270 bp PstI-HindIII fragment. The resulting recombinant plasmid pZU-A carries the 35S promoter, a unique PstI site and the NOS terminator (FIG. 7). The sequence of the used 35S promoter in the plant expression vector pZU-A is as follows:

```
  1 AAGCTTCTAG AGATCCGTCA ACATGGTGGA GCACGACACT CTCGTCTACT

51 CCAAGAATAT CAAAGATACA GTCTCAGAAG ACCAAAGGGC TATTGAGACT

101 TTTCAACAAA GGGTAATATC CGGAAACCTC CTCGGATTCC ATTGCCCAGC

151 TATCTGTCAC TTCATCAAAA GGACAGTAGA AAAGGAAGGT GGCACCTACA

201 AATGCCATCA TTGCGATAAA GGAAAGGCTA TCGTTCAAGA TGCCTCTGCC

251 GACAGTGGTC CCAAAGATGG ACCCCCACCC ACGAGGAGCA TCGTGGAAAA

301 AGAAGACGTT CCAACCACGT CTTCAAAGCA AGTGGATTGA TGTGATATCT

351 CCACTGACGT AAGGGATGAC GCACAATCCC ACTATCCTTC GCAAGACCCT

401 TCCTCTATAT AAGGAAGTTC ATTTCATTGG AGAGGACCCT GCAG
```

Figure 5B:
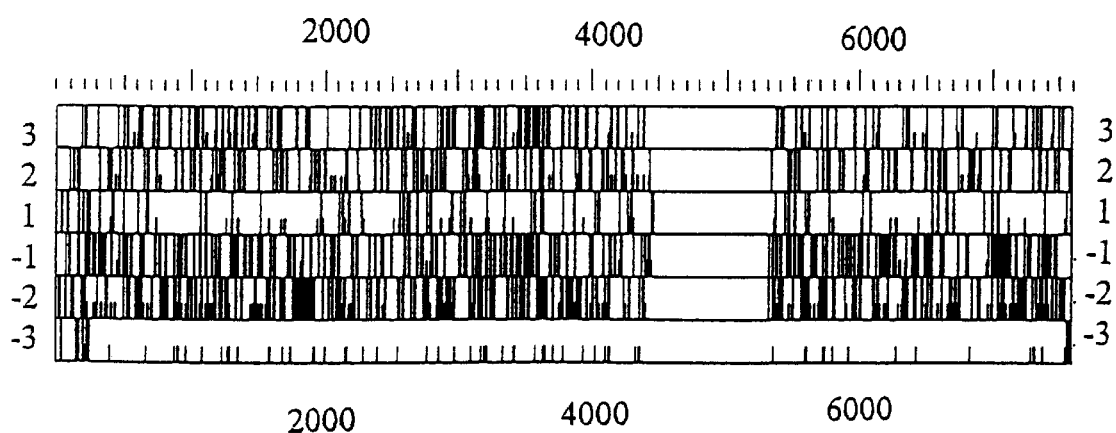
Figure 5C:
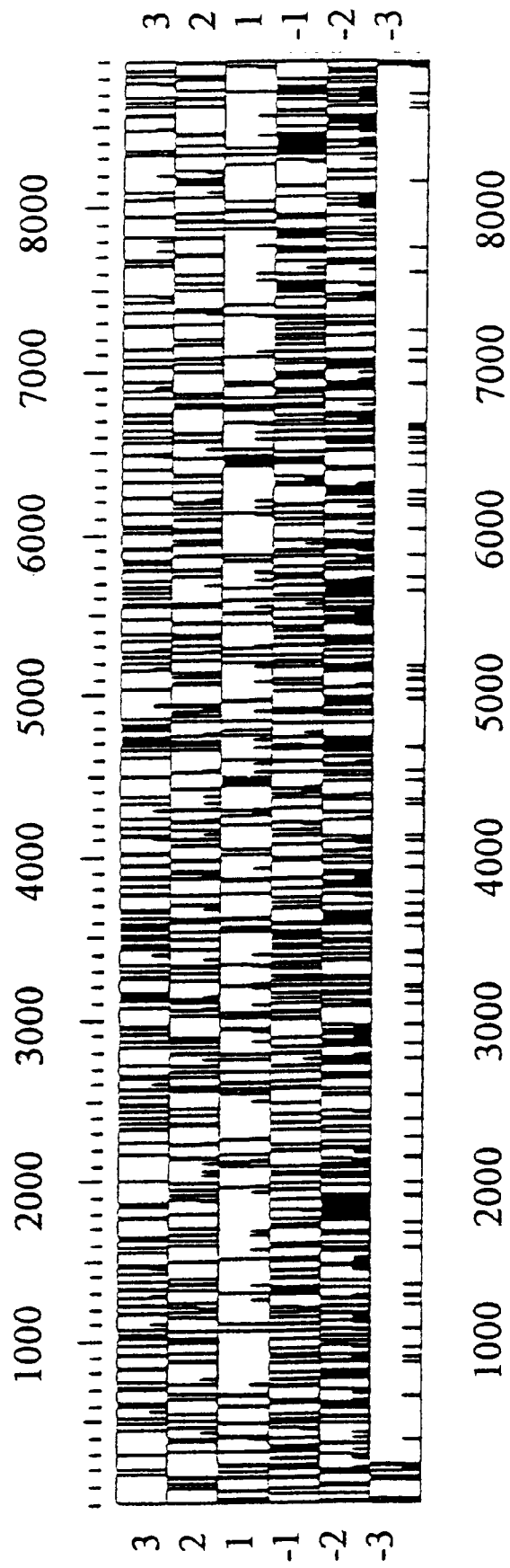

FIG. 3 shows the cloning strategy for the L RNA derived, overlapping cDNA clones. Summarized sequence data of the TSWV M and L RNA are given in FIG. 6A and 6B respectively. Computer simulated translation suggests that this viral L RNA is of negative polarity containing one single open reading frame which starts 34 nucleotides from the 3'-end of the viral RNA and stops at nucleotide 236 from the 5'-end of the viral RNA (FIG. 5B). The mRNA (complementary to the viral L RNA) containing this open reading frame is most probably translated into the viral transcriptase.

The complete sequence from the used NOS terminator in the vector pZU-A is as follows:

```
  1 CTGCAGATCG TTCAAACATT TGGCAATAAA GTTTCTTAAG ATTGAATCCT

51 GTTGCCGGTC TTGCGATGAT TATCATATAA TTTCTGTTGA ATTACGTTAA

101 GCATGTAATA ATTAACATGT AATGCATGAC GTTATTTATG AGATGGGTTT

151 TTATGATTAG AGTCCCGCAA TTATACATTT AATACGCGAT AGAAAACAAA

201 ATATAGCGCG CAACCTAGGA TAAATTATCG CGCGCGGTGT CATCTATGTT

251 ACTAGATCTC TAGAAAGCTT
```

Example 6

Construction of an Expression Vector pZU-B

The recombinant plasmid pZO347 is a derivative of pBluescript carrying a 496 bp BamHI-SmaI fragment containing a 426 bp 35S promoter fragment (HincII fragment) of CaMV strain Cabb-S, linked to a 67 bp fragment of the non-translated leader region, the so-called Ω-region, of the tobacco mosaic virus. This results in a chimeric promoter with a complete transcriptional fusion between the promoter of CaMV to the untranslated leader of TMV. By using in vitro mutagenesis the original position of the TMV ATG startcodon is mutated to a SmaI site.

The plasmid pZO008 carries the nopaline synthase (NOS) terminator as a 260 bp PstI-HindIII fragment. This PstI-HindIII fragment is excised from pZO008 and ligated using T4 ligase into PstI-HindIII linearized pZO347. The resulting recombinant plasmid pZU-B is another plant expression vector. The sequence of this 35S-Ω promoter as used in the plant expression vector pZU-B is as follows:

```
  1 GGATCCGGAA CATGGTGGAG CACGACACGC TTGTCTACTC CAAAAATATC

51 AAAGATACAG TCTCAGAAGA CCAAAGGGCA ATTGAGACTT TTCAACAAAG

101 TTATTGTGAA GATAGTGGAA AAGGAAGGTG GCTCCTACAA ATGCCATCAT

151 TGCGATAAAG GAAAGGCCAT CGTTGAAGAT GCCTCTGCCG ACAGTGGTCC

201 CAAAGATGGA CCCCCACCCA CGAGGAGCAT CGTGGAAAAA GAAGACGTTC

251 CAACCACGTC TTCAAAGCAA GTGGATTGAT GTGATATCTC CACTGACGTA

301 AGGGATGACG CACAATCCCA CTATCCTTCG CAAGACCCTT CCTCTATATA

351 AGGAAGTTCA TTTCATTTGG AGAGGACTTT TTACAACAAT TACCAACAAC

401 AACAAACAAC AAACAACATT ACAATTACTA TTTACAATTA CCCGGG
```

Figure 8:
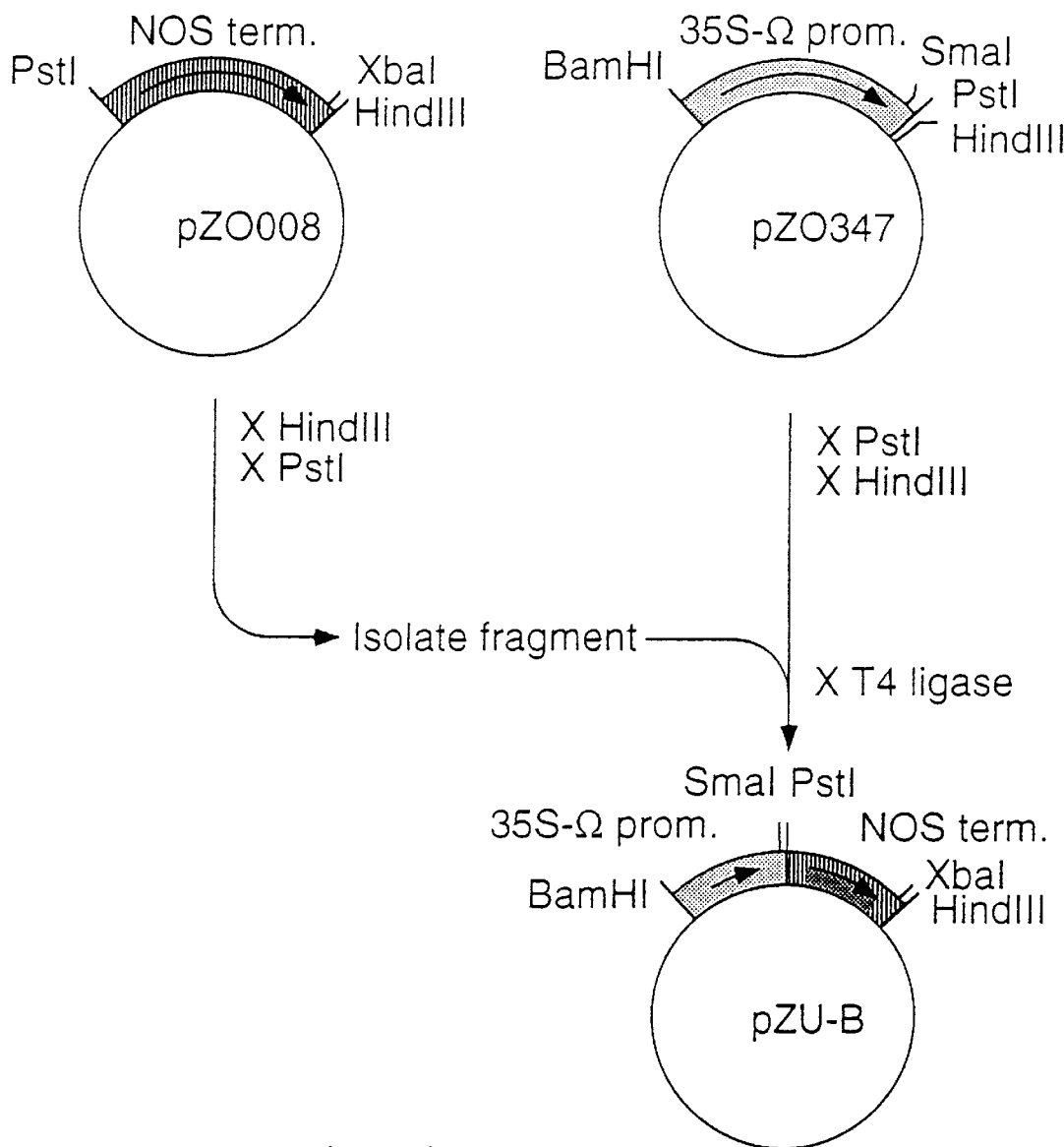

The resulting recombinant plasmid pZU-B contains the 35S HindII-TMV Ω fusion (35S-Ω), unique SmaI and PstI sites and the NOS terminator (FIG. 8). This expression vector is preferentially used in constructing translational fusions of the gene to be expressed downstream of the chimeric promoter 35S-Ω.

Example 7

Subcloning of the TSWV-N Protein Gene

Figure 2:
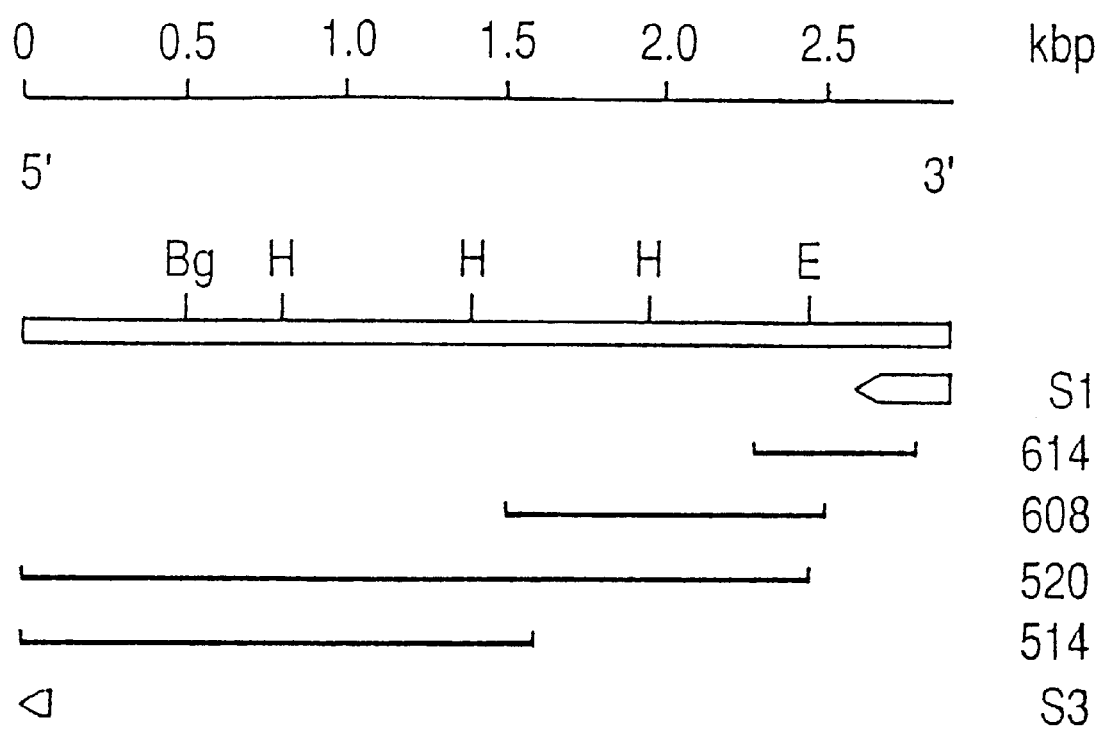
Figure 3:
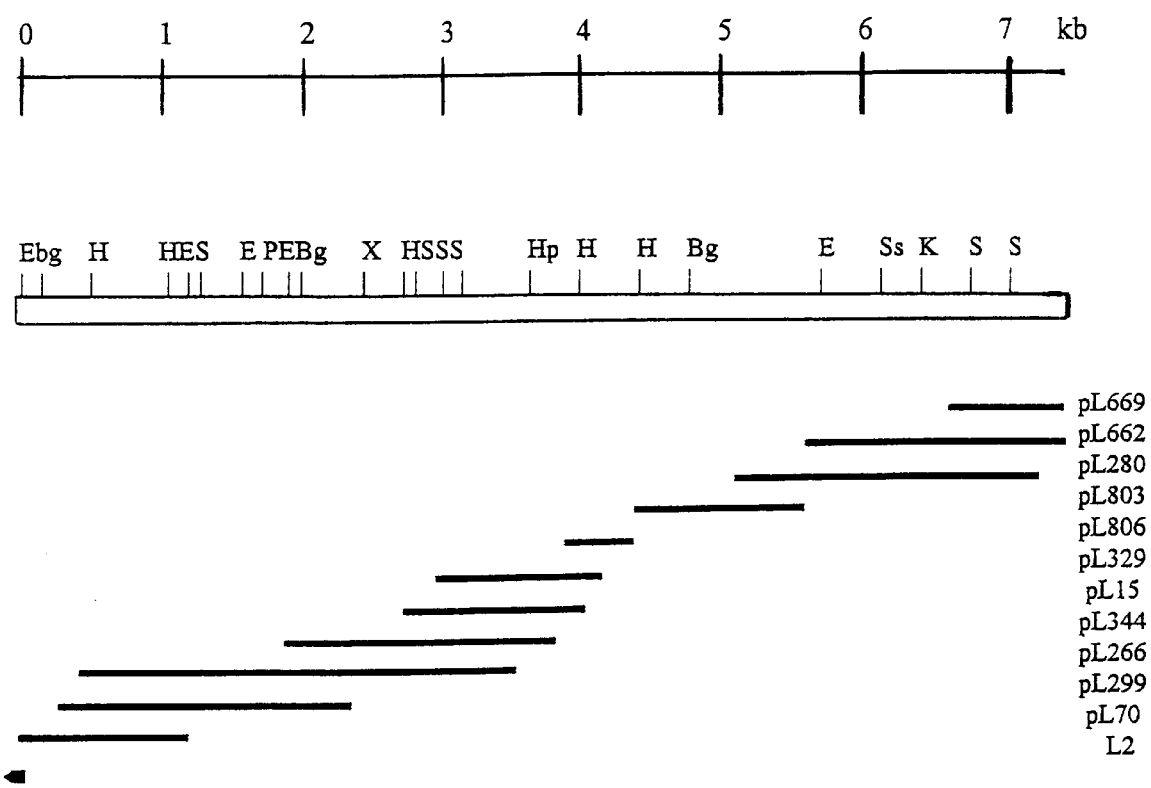
Figure 9:
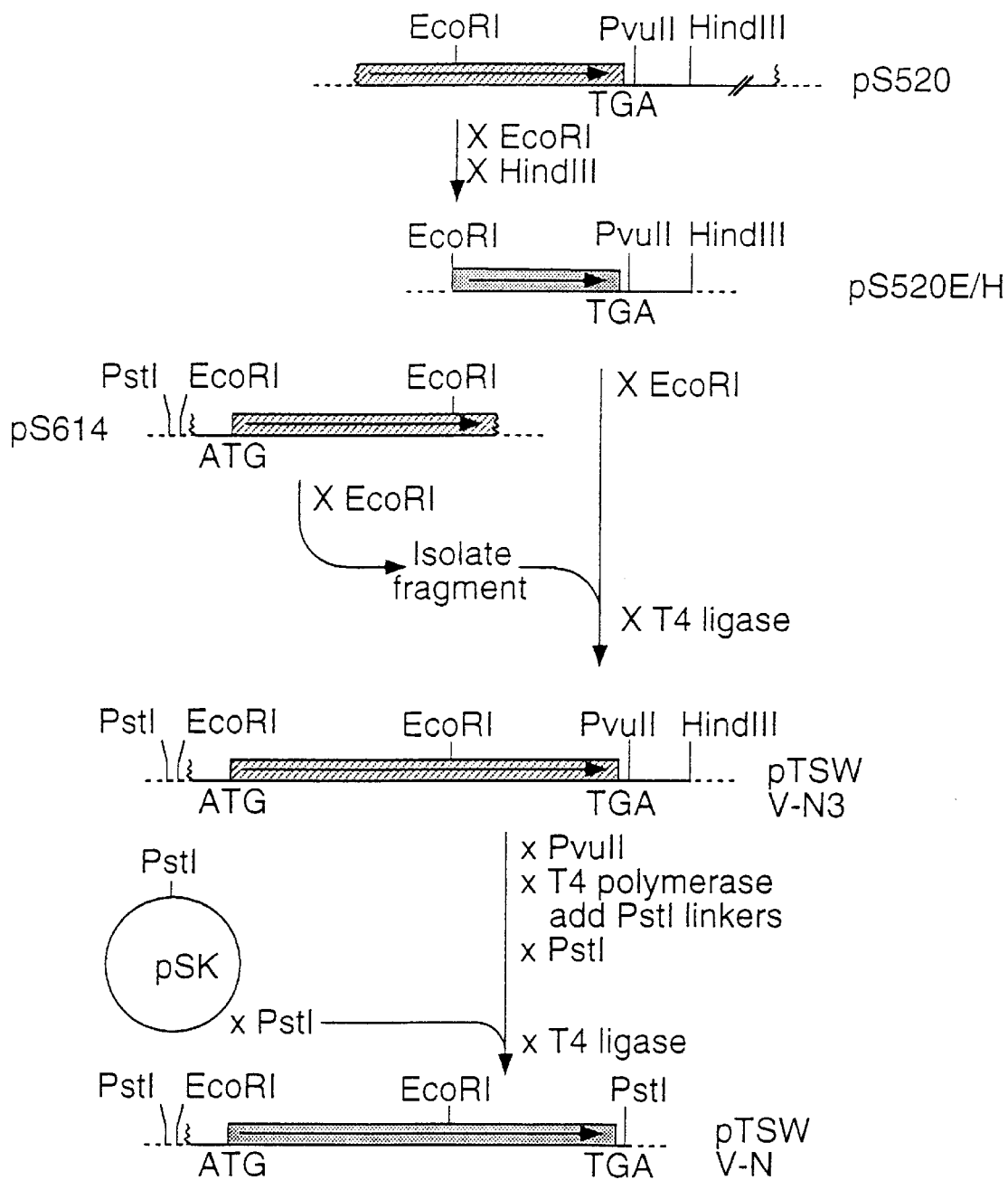

The TSWV-N protein coding sequence is obtained by fusion of the cDNA clones pS614 and pS520 (see FIG. 2). The cDNA clone pS520 is subjected to EcoRI-HindIII double-digestion and the fragment containing the 3'-end of the TSWV-N protein gene is separated electrophoretically and purified from the gel using a DEAE membrane (NA-45, Schleicher and Schüll) and cloned in the EcoRI-HindIII linearized pBluescript (Stratagene) resulting in the recombinant plasmid pS520E/H. The 5=-end containing fragment of the TSWV-N protein is excised from pS614 by a EcoRI digestion. This fragment is separated electrophoretically and purified from the gel using a DEAE membrane (NA-45, Schleicher and Schüll) and cloned in the EcoRI linearized pS520E/H resulting in the recombinant plasmid pTSWV-N3. The TSWV-N gene containing plasmid pTSWV-N3 is linearized by digestion with PvuII PstI linkers 5' d(CCTGCAGG) are ligated with T4 ligase to the blunt ends of the linear DNA. Subsequently, the DNA is digested with PstI and the fragment containing the TSWV-N protein sequence is separated electrophoretically and excised from the gel. The TSWV-N protein gene containing fragment is ligated into a PStI linearized vector such as pBluescript (Stratagene) to yield the recombinant plasmid pTSWV-N (FIG. 9). This addition of restriction sites facilitates the construction of further plasmids (Alternatively, one may choose to add the sites in different ways such as but not limited to site-directed mutagenesis or by ligation of other synthetic oligonucleotide linkers. These methods are all known to a person skilled in the art.)

Example 8

Subcloning of the TSWV Non-Structural Protein Gene (NSs-Gene) of the TSWV S RNA

Figure 10:
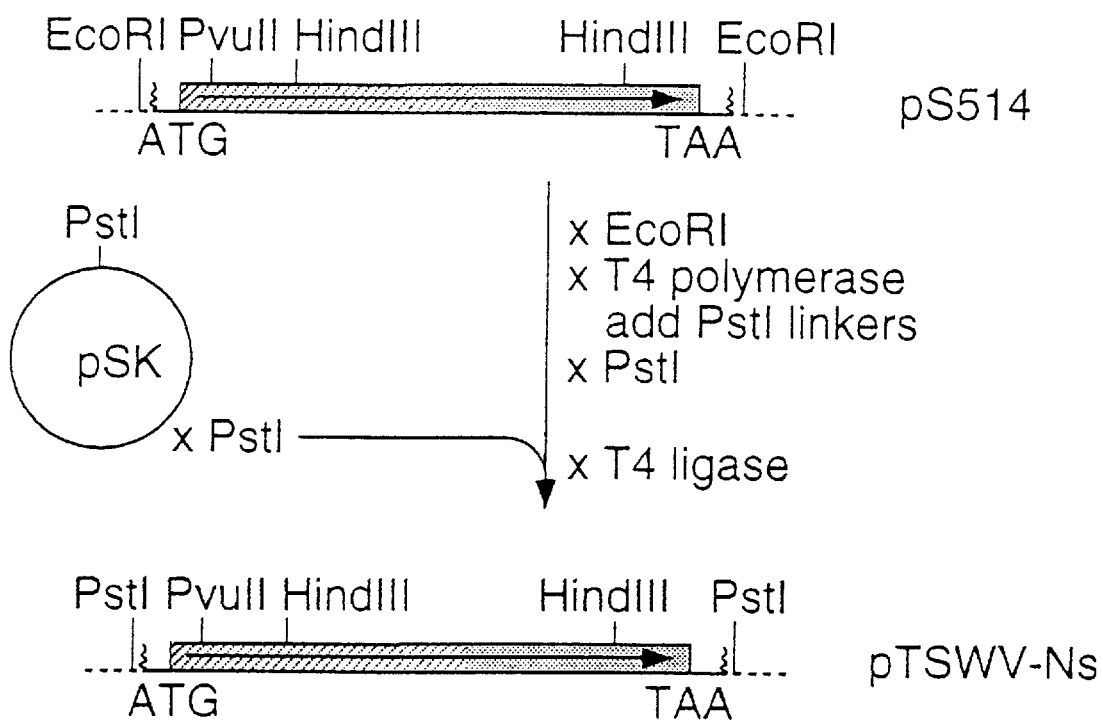

The sequence of the non-structural protein NSs is isolated from the cDNA clone pS514. The NSs-protein gene is located on an EcoRI fragment. After restriction of the cDNA clone pS514 with EcoRI and treatment with T4 DNA polymerase to create blunt ends. The NSs gene containing fragment is separated electrophoretically on an agarose gel and excised from the gel. To this blunt ended fragment containing the NSs-protein gene synthetic PstI linkers (5' d(CCTGCAGG)-3') are ligated using T4 polymerase. After restriction with PstI, the NSs-protein gene containing fragment is ligated in an PstI linearized pBluescript to yield the recombinant plasmid pTSWV-NSs (FIG. 10).

Example 9

Construction of Plant Transformation Vectors Containing TSWV Sequences

Example 9A: N-Protein Gene Constructions in pZU-A

Figure 11:
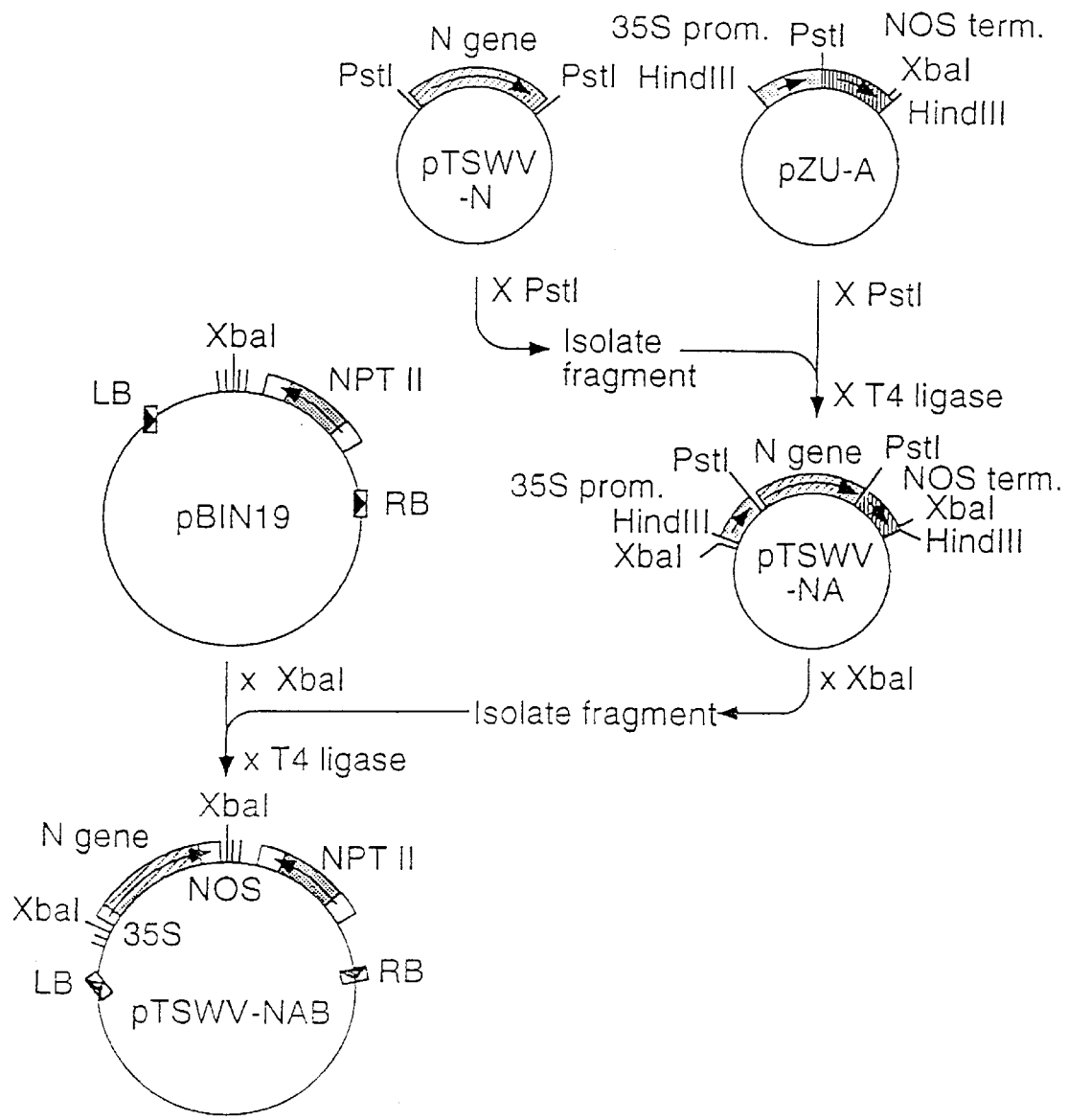

In order to create a plant transformation vector containing the N protein gene driven by the 35S promoter and terminated by the NOS terminator, the PstI fragment of pTSWV-N is isolated and inserted into PstI linearized pZU-A thereby creating the chimeric gene cassette vector pTSWV-NA. The cassette containing the 35S promoter, the N-protein gene and the NOS terminator is excised from pTSWV-NA by restriction with XbaI and ligated in the unique XbaI site of pBIN19, a binary transformation vector developed by Bevan et al (1984). The resulting plasmid pTSWV-NAB (FIG. 11) is used in plant transformation experiments using methods well known to a person skilled in the art.

Example 9B: N-Protein Construction in pZU-B

Figure 12:
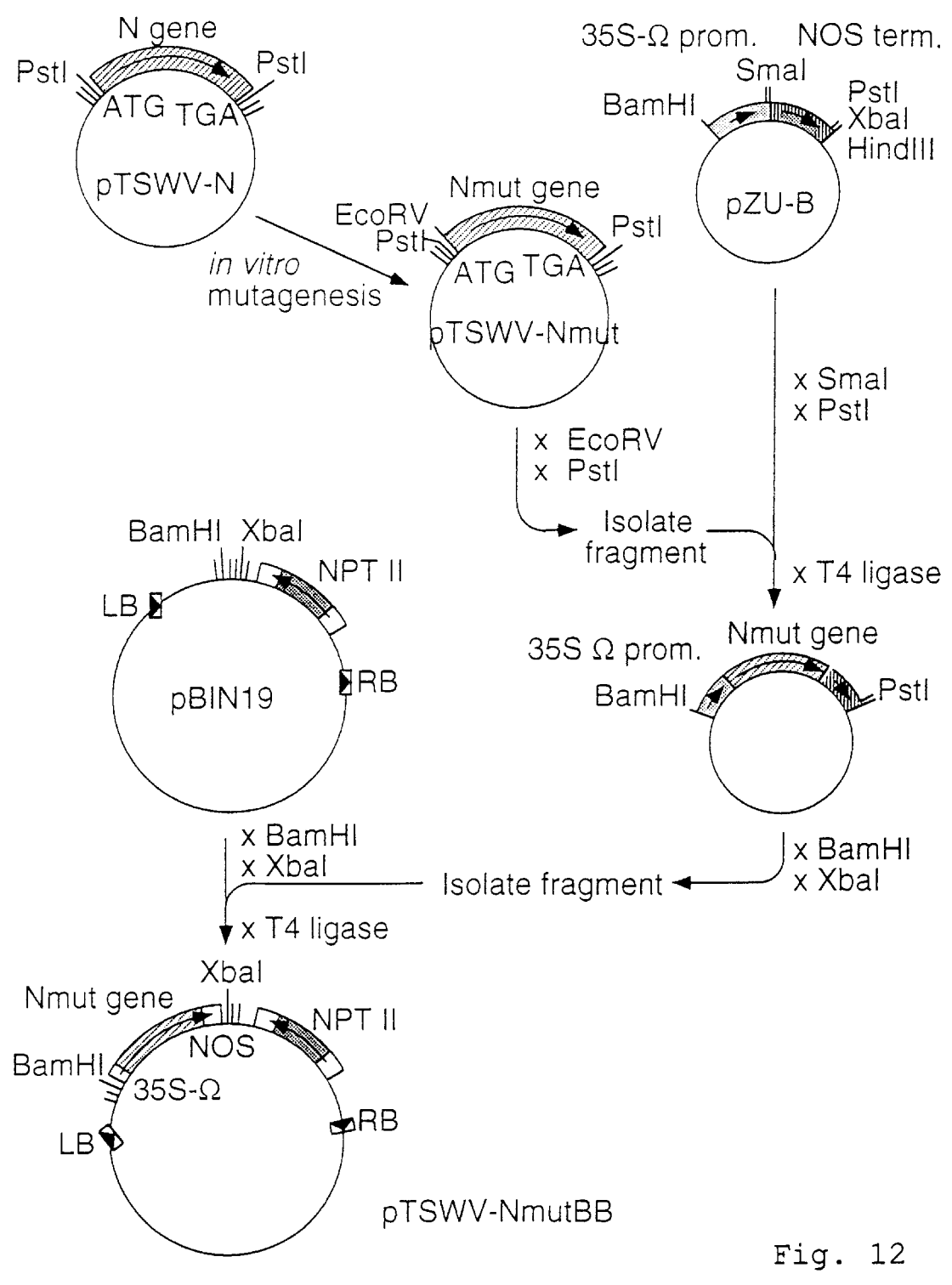

In order to make a fusion in which the ATG start codon from the N protein gene is fused directly to the 3'-end of the TMV untranslated leader of the 35S-Ω promoter the startcodon of the N gene has to be mutated. Using site-direction mutagenesis, the sequence 5' d(ACGATCATC<u>ATG</u>TCT) in pTSWV-N is mutated to 5' d(ACGATATC<u>ATG</u>TCT), thereby creating an EcoRV site: 5' d(GATACT) just proximal to the ATG startcodon of the N gene. The resulting recombinant plasmid is called pTSWV-Nmut. The mutated N protein gene is excised from this plasmid via an EcoRV-PstI digestion. This fragment is isolated and inserted into the SmaI-PstI linearized pZU-B, resulting in recombinant plasmid pTSWV-NmutB. The chimeric cassette containing the 35S-Ω promoter, the mutated N gene and the NOS terminator is excised from the plasmid pTSWV-NmutB via a BamHI/XbaI digestion. The isolated chimeric gene cassette is then inserted into the BamHI/XbaI linearized pBIN19 to create the binary transformation vector pTSWV-NmutBB. The resulting plasmid pTSWV-NmutBB (FIG. 12) is used in plant transformation experiments using methods well known to a person skilled in the art.

Example 9C: NSs-Protein Gene Constructions in pZU-A

Figure 13:
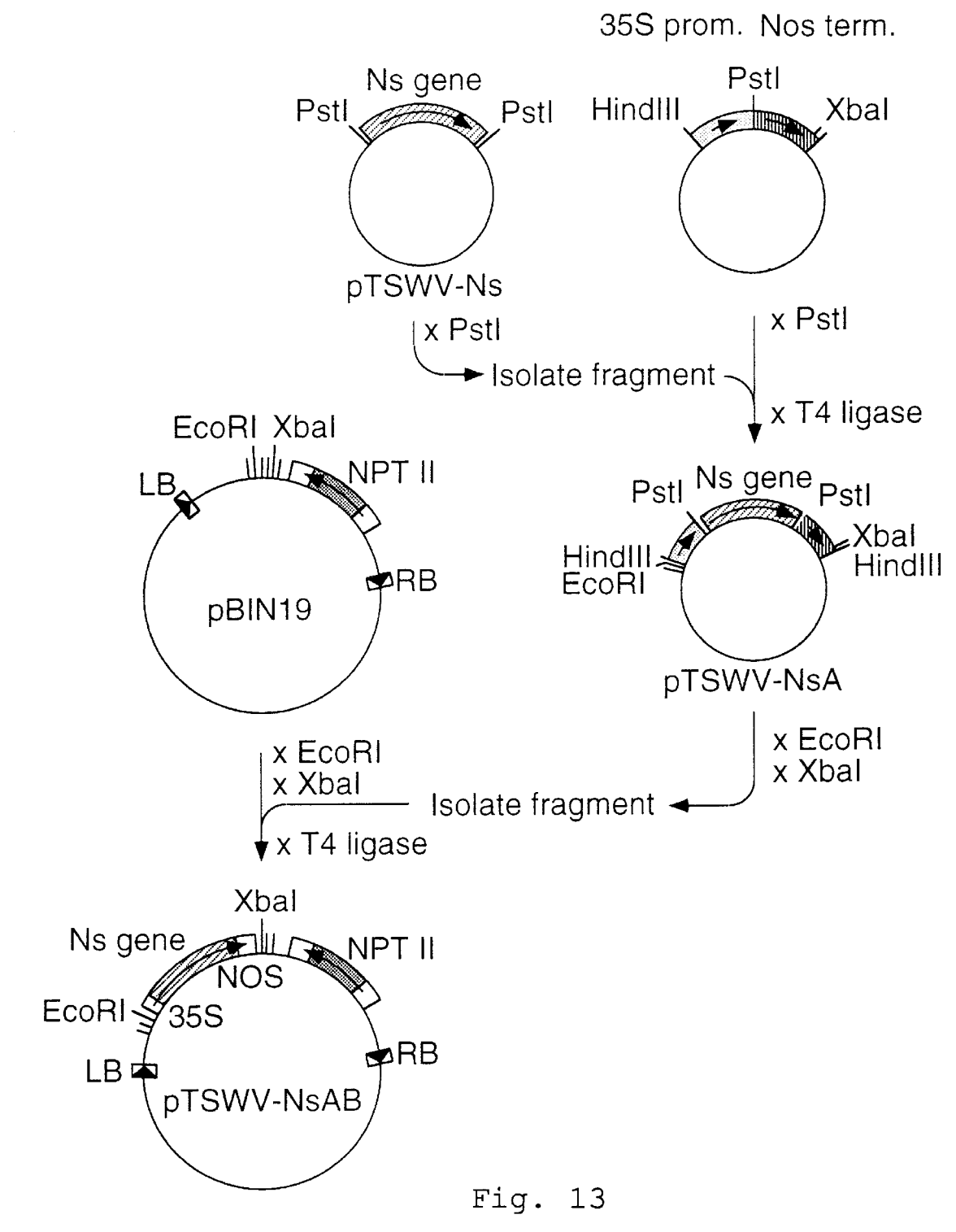

In order to create a plant transformation vector containing the NSs-protein gene driven by the 35S promoter and terminated by the NOS terminator, the PstI fragment of pTSWV-NSs is isolated and inserted into PstI linearized pZU-B to create the chimeric gene cassette vector pTSWV-NsA. The cassette containing the 35S promoter, the NSs-protein gene and the NOS terminator is excised from pTSWV-NsA by restriction with EcoRI and XbaI and ligated into EcoRI-XbaI linearized pBIN19. The resulting plasmid pTSWV-NsAB (FIG. 13) is used in plant transformation experiments using methods well known to a person skilled in the art.

Example 9D: NSs-Protein Gene Constructions in pZU-B

Figure 14:
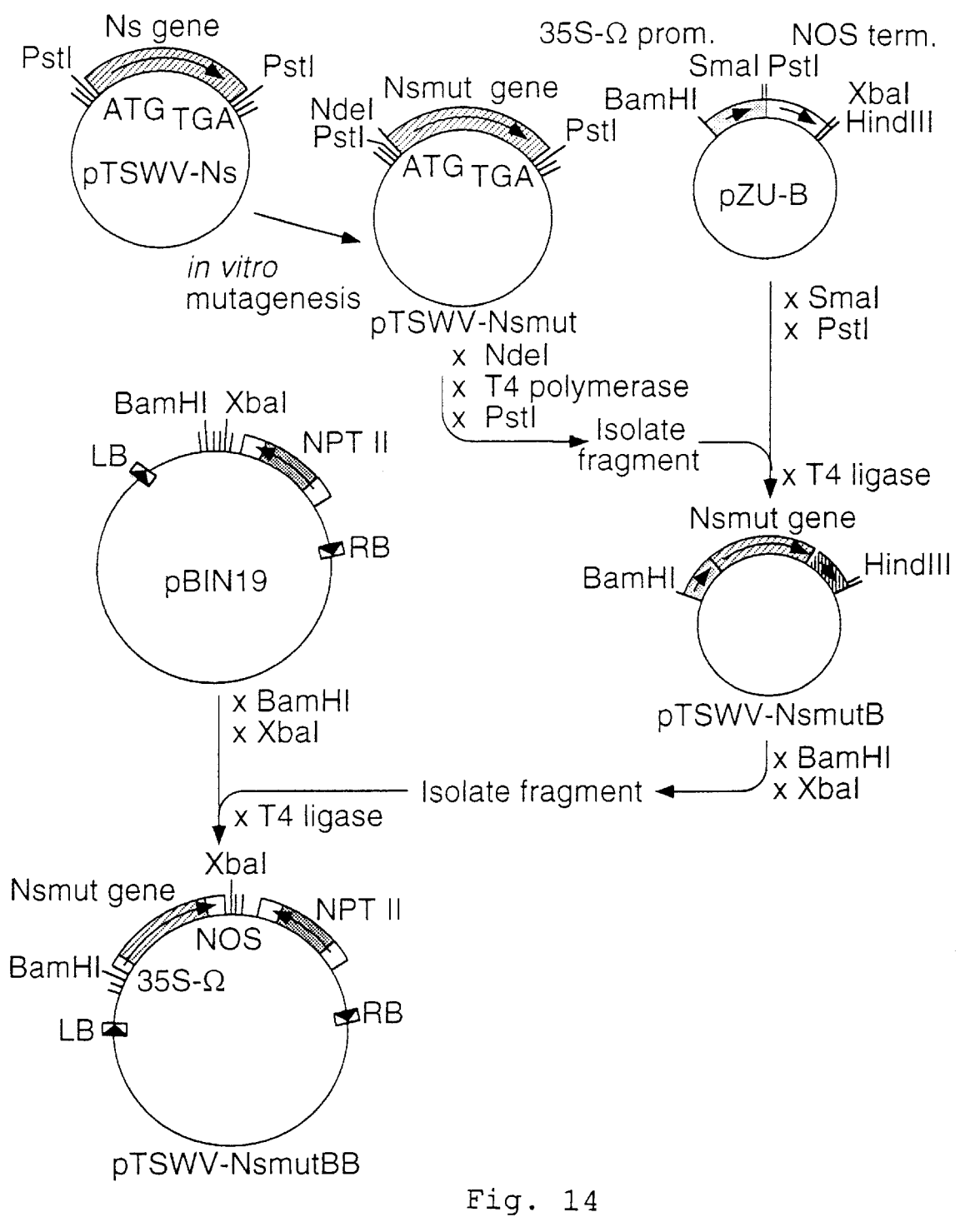

In order to create a fusion in which the ATG start codon from the NSs-protein is fused directly to the 3'-end of the TMV leader of the 35S-Ω promoter the startcodon of the NSs gene has to be mutated. Using site-directed mutagenesis, a procedure known to a person skilled in the art, the sequence 5' d(AACCATA<u>A</u>TGTCT) is mutated to 5' d(AACCAT<u>ATG</u>TCT), thereby creating a NdeI site: 5' d(CAT<u>ATG</u>) that includes the ATG startcodon of the NSs-protein gene. The resulting plasmid is called pTSWV-NSsmut. The plasmid pTSWV-NSsmut is linearized with NdeI, followed by a treatment with T4 DNA polymerase to create blunt ends. This linearized DNA is digested with PstI and the fragment containing the mutated NSs gene is isolated and inserted into SmaI PstI linearized pZU-B resulting in the recombinant plasmid pTSWV-NsmutB. The chimeric cassette containing the 35S-Ω promoter, the mutated NSs-protein gene and the NOS terminator is excised from the plasmid pTSWV-NsmutB via a BamHI/XbaI digestion. The isolated chimeric gene cassette is then inserted into the BamHI/XbaI linearized pBIN19 to create the binary transformation vector pTSWV-NsmutBB. The resulting plasmid pTSWV-NsmutBB (FIG. 14) is used in plant transformation experiments using methods well known to a person skilled in the art.

Example 9E: 5'- and 3'-termini "Pan-Handle" Constructions in pZU-A and pZU-B

Figures 15, 15A, 15B, 15C:
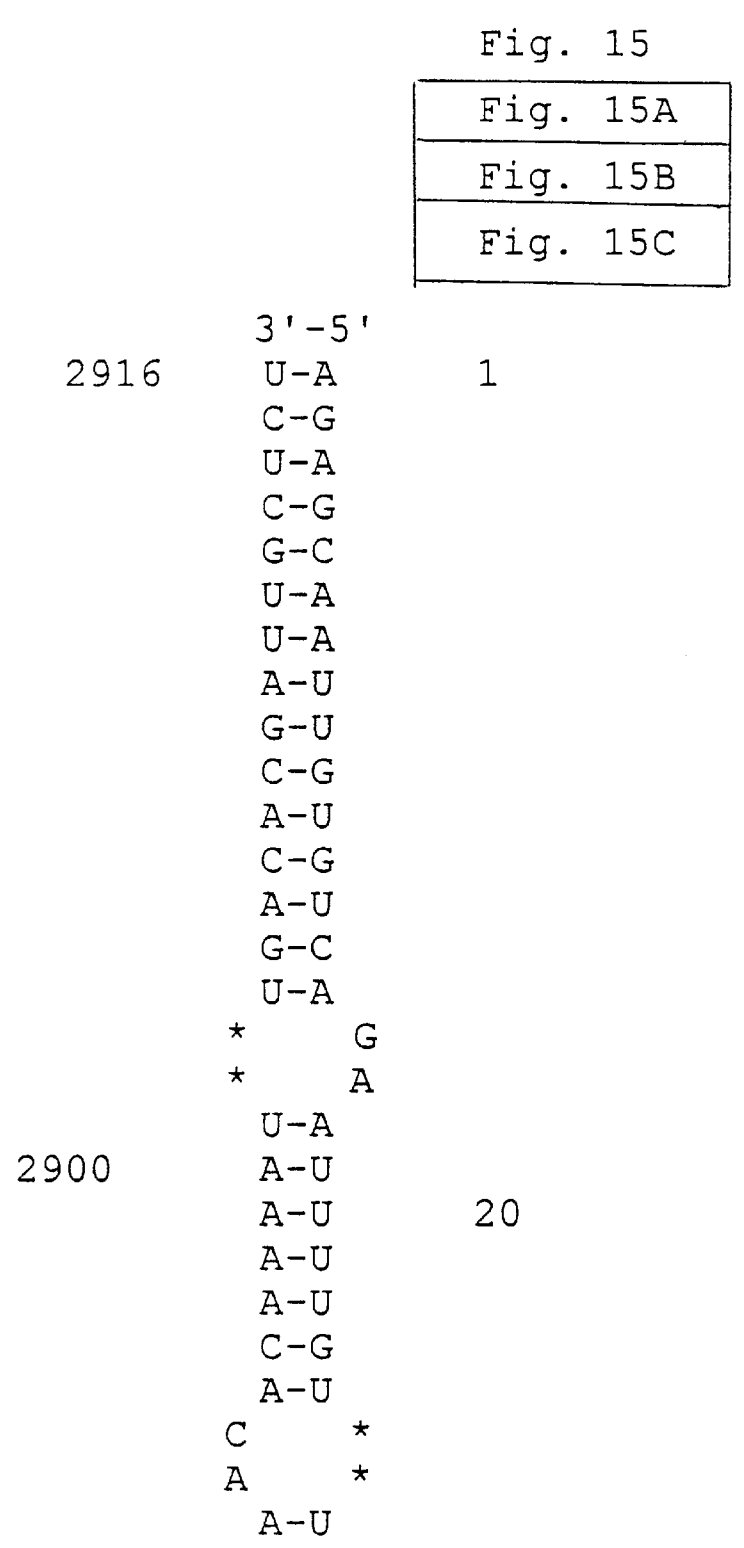
Figure 15B:
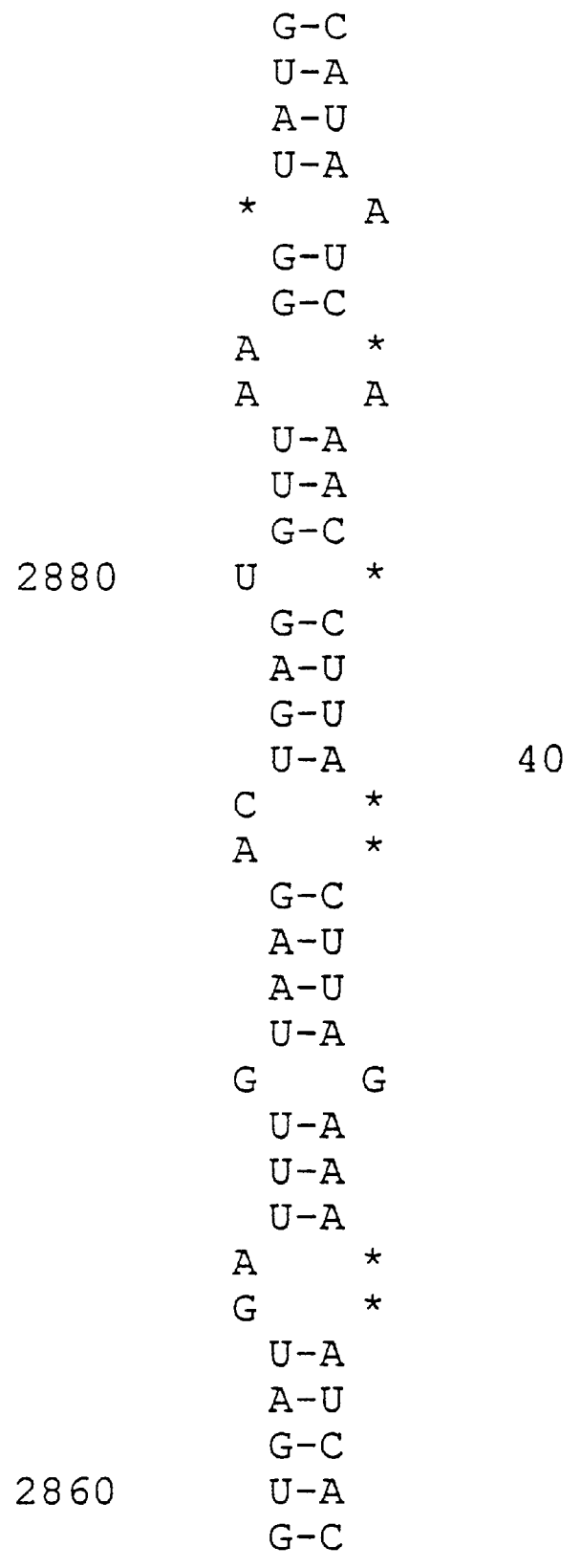
Figure 15C:
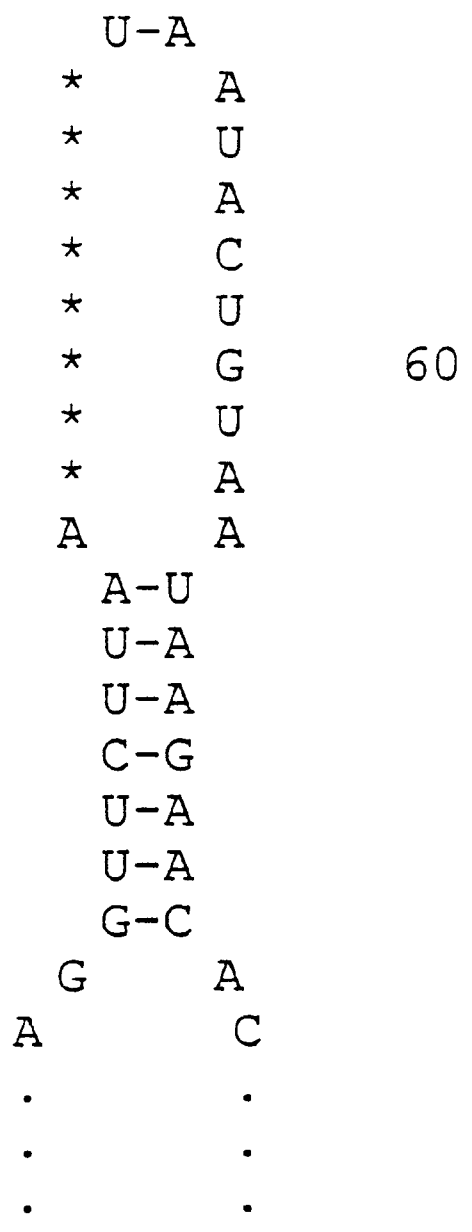

A DNA analysis programme is used to locate the "pan-handle" loop in the viral TSWV S RNA. The strongest "pan-handle" loop that is detected includes the first 70 nucleotides at the 5'-end (1 to 70) of the viral S RNA and the last 67 nucleotides at the 3'-end (2850 to 2916) of the viral S RNA (FIG. 15). The DNA sequence containing this "pan-handle" loop in the viral S RNA is as follows:

```
   1 AGAGCAATTG TGTCAGAATT TTGTTCATAA TCAAACCTCA CTTAGAAAAT

51 CACAATACTG TAATAAGAAC
``` and

```
2850 GTTCTTAATG TGATGATTTG TAAGACTGAG TGTTAAGGTA TGAACACAAA

2900 ATTGACACGA TTGCTCT
```

A DNA analysis programme is used to locate the "pan-handle" loop in the viral TSWVL RNA. A strong "pan-handle" loop that is detected includes the first 80 nucleotides at the 5'-end (1 to 80) of the viral L RNA and the last 80 nucleotides at the 3'-end of the viral L RNA. The DNA sequence containing this "pan-handle" loop in the viral L RNA is as follows:

```
   1 AGAGCAATCA GGTACAACTA AAACATATAA CCTCTCCACA GCCAGACTTT

51 ACAAATTACA TAAGAATTCC CTCCAGTGAA
``` and

```
     AAAGTGGTTC CATTTTCTAT TAATTTTTGT ATTTTCTGGA TGTTCATGTT

TGCTTAAAAT CGTTGTTACC TGATTGCTCT
```

These regions are synthesized on a commercial DNA synthesizer and appropriate linker sequences are added. Construction of the "pan-handle" vectors of S and L RNA results in respectively: pTSWV-termS and pTSWV-termL. Using appropriate restriction enzyme combination these fragments are inserted between the CaMV 35S promoter and the NOS terminator of pZU-A or between the 35S-Ω promoter and the NOS terminator of pZU-B yielding the chimeric cassettes: pTSWV-termSA, pTSWV-termLA, pTSWV-termSB and pTSWV-termLB. These cassettes are then transferred into the binary transformation vector pBIN19 using appropriate enzyme combinations yielding the following plasmids: pTSWV-termSAB, pTSWV-termLAB, pTSWV-termSBB and pTSWV-termLBB. Alternatively, it is possible to design "pan-handle" constructs including the 3'- and 5'-end termini that are larger as indicated above, or separated by any other DNA sequence in order to enhance the stability of the transcripts produced from these recombinant genes in plants. All "pan-handle" constructs resemble shortened tospovirus RNA, respectively TSWV RNA molecules and therefore can be regarded as defective interfering RNAs.

Figures 16, 16A, 16B:
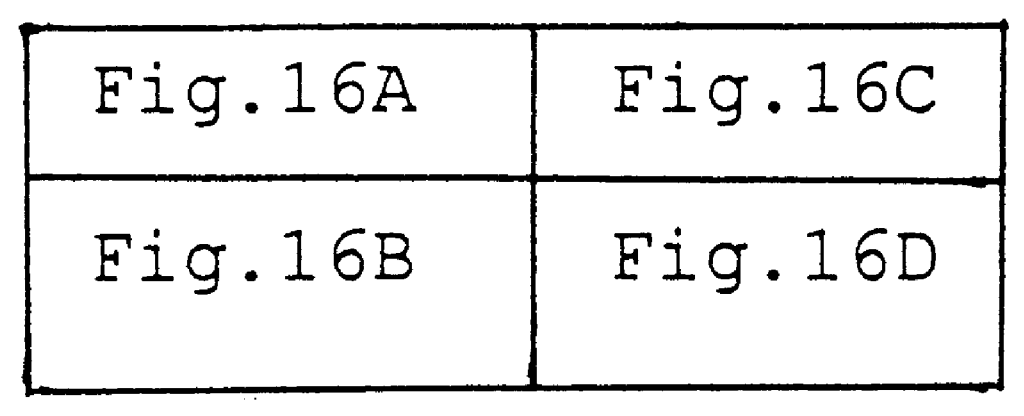
Figure 16A:
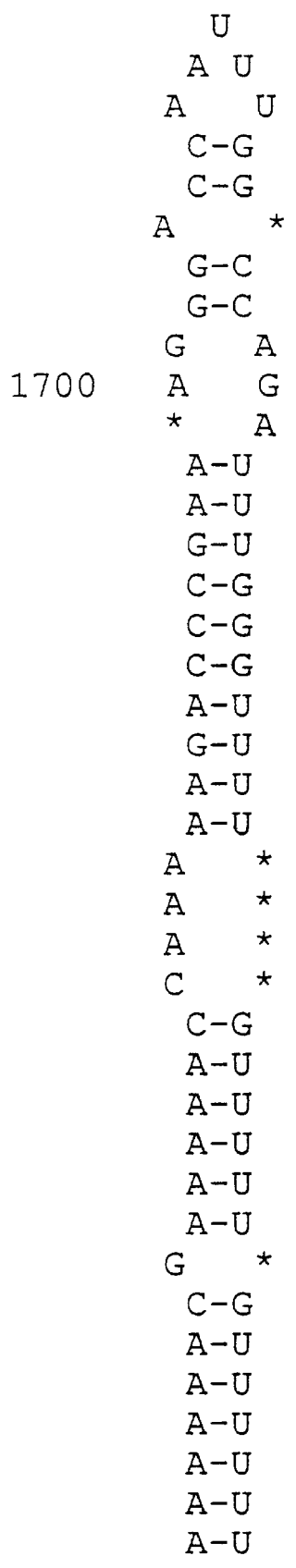
Figure 16B:
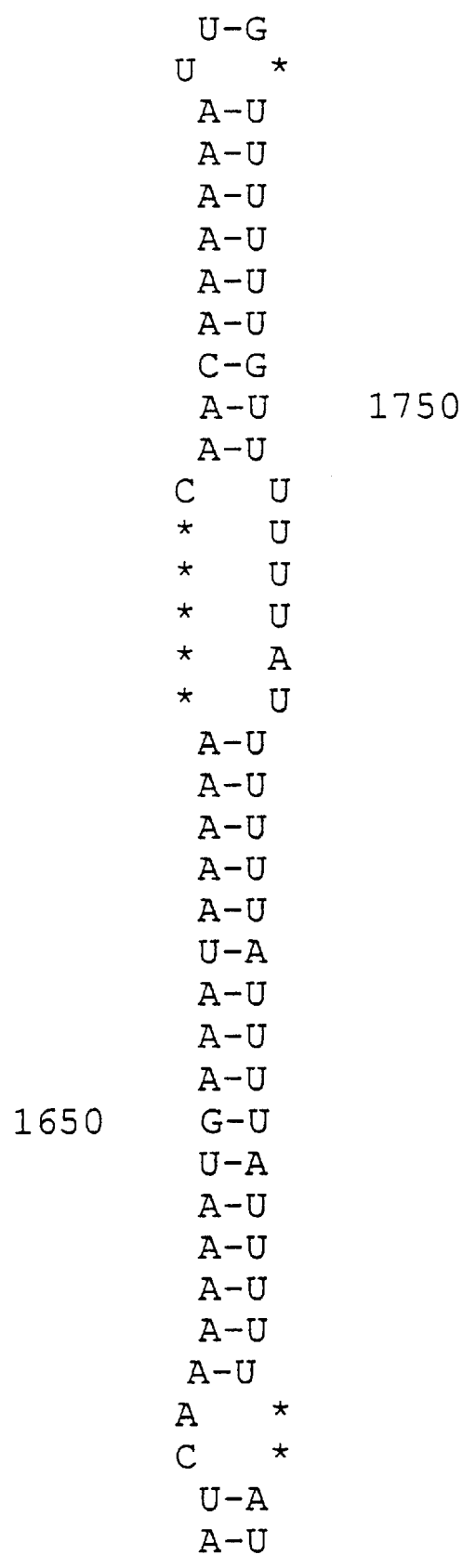
Figure 16C:
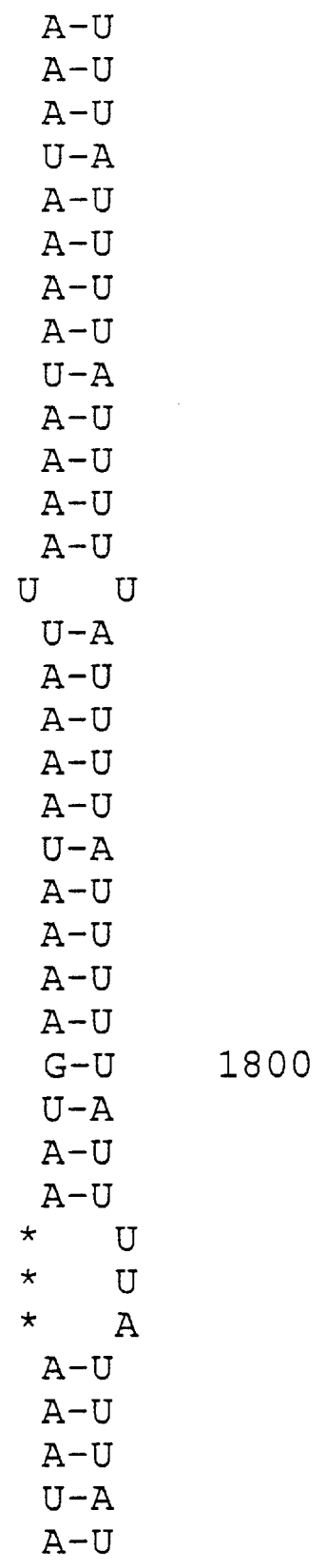
Figure 16D:
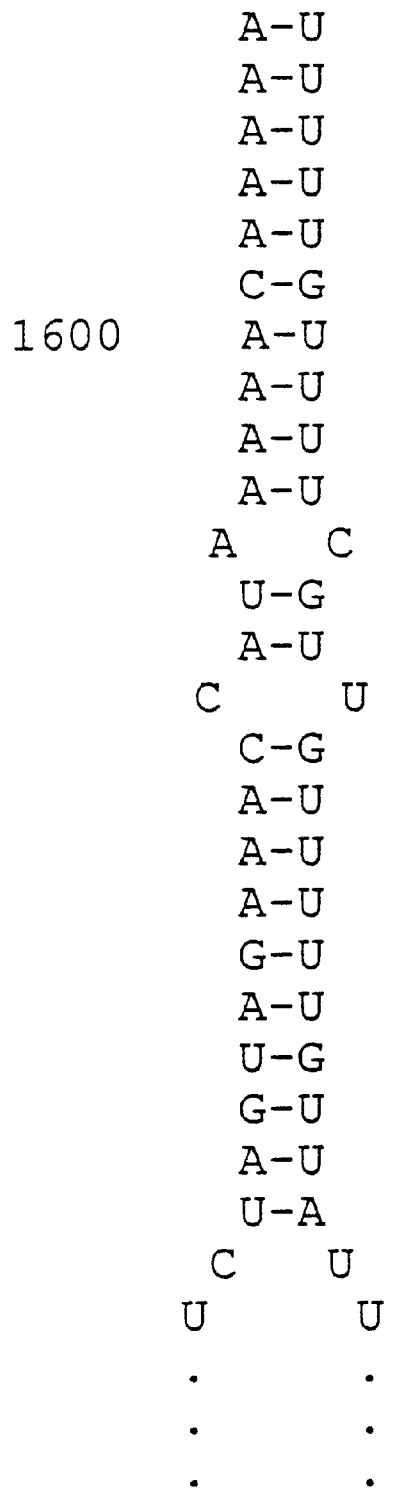

Example 9F: Construction Containing TSWV S RNA Hairpin Region in pZU-A and pZU-B A DNA analysis programme is used to locate the hairpin loop in the viral TSWV S RNA. The strongest hairpin loop that is detected starts at nucleotide 1592 and ends at nucleotide 1834 (FIG. 16). The sequence containing this hairpin loop is as follows:

```
  1 TAGTAGAAAC CATAAAAACA AAAAATAAAA ATGAAAATAA AATTAAAATA

51 AAATAAAATC AAAAAATGAA ATAAAAACAA CAAAAAATTA AAAAACGAAA

101 AACCAAAAAG ACCCGAAAGG GACCAATTTG GCCAAATTTG GGTTTTGTTT

151 TTGTTTTTTG TTTTTTGTTT TTTATTTTTT ATTTTATTTT TATTTTATTT

201 TATTTTTATT TTATTTTTAT TTTATTTATT TTTTGTTTTC GTTGTTTTTG

251 TTA
```

A HindIII fragment of 526 bp carrying the hairpin region is isolated from pS514. This fragment is excised from a agarose gel and subsequently treated with T4 polymerase to create blunt ends. In the following step PstI linkers are ligated to these blunt ends. After digestion with PstI the fragment is cloned in PstI linearized pZU-A, resulting in the recombinant plasmid pTSWV-HpSA. The plasmid pTSWV-HpSA is digested with HindIII and the fragment containing the chimeric gene is excised from an agarose gel and ligated into HindIII linearized pBIN19, resulting in the transformation vector pTSWV-HpSAB.

Alternatively, the HindIII fragment of pS514 is treated with T4 DNA polymerase to create blunt ends and is subsequently cloned in the SmaI site of the expression vector pZU-B, resulting in the recombinant plasmid pTSWV-HpSB. The plasmid pTSWV-HpSB is digested with HindIII and the fragment containing the chimeric gene is excised from an agarose gel and ligated into XbaI linearized pBIN19, resulting in the transformation vector pTSWV-HpSBB.

(It is clear to a person skilled in the art that also other fragments can be isolated from the cDNA clones of the TSWV S RNA containing the hairpin region as described above without interference with the function. Also, a fragment containing the hairpin region may be synthesized using a DNA-synthesizer.)

Example 10

Transformation of Binary Vectors to Plant Material

Methods to transfer binary vectors to plant material are well established and known to a person skilled in the art. Variations in procedures exist due to for instance differences in used Agrobacterium strains, different sources of explant material, differences in regeneration systems depending on as well the cultivar as the plant species used.

The binary plant transformation vectors as described above are used in plant transformation experiments according to the following procedures. The constructed binary vector is transferred by tri-parental mating to an acceptor *Agrobacterium tumefaciens* strain, followed by southern analysis of the ex-conjugants for verification of proper transfer of the construct to the acceptor strain, inoculation and cocultivation of axenic explant material with the *Agrobacterium tumefaciens* strain of choice, selective killing of the *Agrobacterium tumefaciens* strain used with appropriate natibiotics, selections of transformed cells by growing on selective media containing kanamycine, transfer of tissue to shoot-inducing media, transfer of selected shoots to root inducing media, transfer of plantlets to soil, assaying for intactness of the construct by southern analyses of isolated total DNA from the transgenic plant, assaying for proper function of the inserted chimeric gene by northern analysis and/or enzyme assays and western blot analysis of proteins.

Example 11

Expression of TSWV RNA Sequences in Plant Cells

RNA is extracted from leaves of regenerated plants using the following protocol. Grind 200 mg leafmaterial to a find powder in liquid nitrogen. Add 800 $\mu$l RNA extraction buffer (100 mM Tris-HCl (pH 8,0), 500 mM NaCl, 2 mM EDTA, 200 mM β-Mercapto-ethanol, 0,4% SDS) and extract the homogenate with phenol, collect the nucleic acids by alcohol precipitation. Resuspend the nucleic acids in 0,5 ml 10 mM Tris-HCl (pH 8,0) 1 mM EDTA, add LiCl to a final concentration of 2 M, leave on ice for maximal 4 hours and collect the RNA by centrifugation. Resuspend in 400 $\mu$l 10 mM Tris-HCl (pH 8,0), 1 mM EDTA and precipitate with alcohol, finally resuspend in 50 $\mu$l 10 mM Tris-HCl (pH 8,0), 1 mM EDTA. RNAs are separated on glyoxal/agarose gels and blotted to Genescreen as described by van Grinsven et al. (1986). TSWV viral RNA is detected using DNA or RNA probes labeled with [$^{32}$P], [$^{35}$S] or by using non-radioactive labeling techniques. Based on these northern analysis, it is determined to what extent the regenerated plants express the chimeric TSWV genes. EDTA (pH 8.0). The ribonucleic acids are recovered by standard alcohol precipitation. The ribonucleic acid pellet is resuspended in 25 $\mu$l 10 mM Tris-HCl, 1 mM EDTA (pH 8.0).

1 $\mu$l of the purified ribonucleic acids is spotted on a nylon blotting membrane (e.g. Hybond-N, Amersham UK). The presence of TSWV in the plant is detected by standard hybridization, using any part or parts of the sequence isolated from virions or preferentially by designing synthetic oligomers on the basis of disclosed sequence information as a probe. (Alternatively, in vitro transcripts of regions of the TSWV genome are used to detect TSWV Related RNA Sequences in diseased plants.) A diseased plant is diagnosed by the occurrence of hybridization at the dot containing RNA material from the diseased plant.

Figure 17:
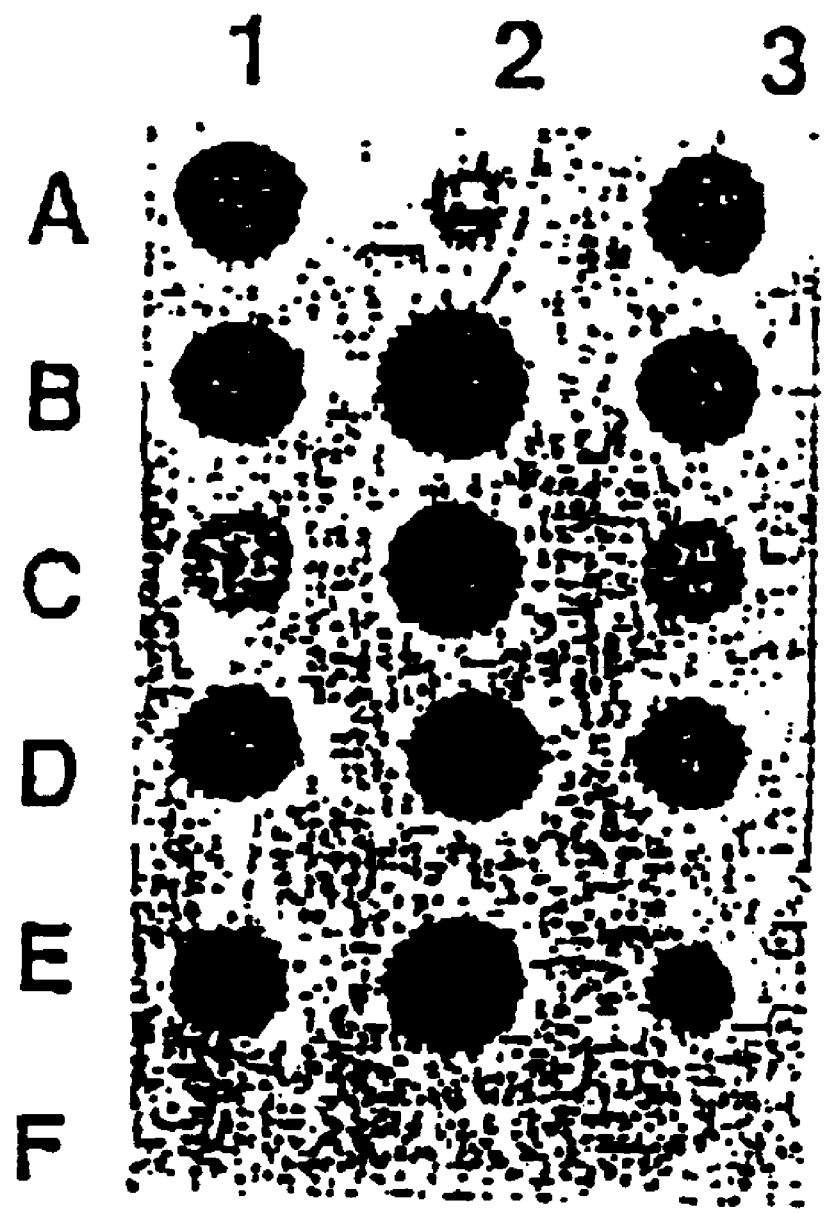
FIG. 17 shows a dot blot analysis of suspected plants.

Using procedures as described herein RNA is isolated from 12 pepper plants (A1–D3) suspected to be virus infected selected from a field. Similarly, RNA is extracted from 3 TSWV inoculated tobacco plants (E1–E3) and from 3 non-inoculated tobacco plants (F1–F3). From each plant an RNA sample of 1 $\mu$l is spotted onto a Hybond membrane. This filter is hybridized under standard conditions with an in vitro transcript synthesized from the cDNA clone pS614 using T3 polymerase and α-[$^{32}$P]UTP as an radioactive label. Control non-infected plants (F1–F3) do not show a signal, control TSWV infected plants (E1–E3) do show a strong signal, whereas suspected pepper plants all show signals ranging in intensity from weak to strong (see FIG. 17).

REFERENCES

Able P P, Nelson R S, De B, Hoffmann N, Rogers S G, Fraley R T and Beachy R N (1986) Delay of disease development in transgenic plants that express the tobacco mosaic virus coat protein gene. Science 232, 738–743.

Ausubel F M, Brent R, Kingston R E, Moore D D, Seidman J G, Smith J A, Struhl K (1987) Current protocols in molecular biology. Green Publishing Associates and Wiley Intersciences, New York, Chichester, Brisbane, Toronto and Singapore.

Beachy R N, Fraley R T and Rogers S G, EP 0 223 452 Protection of plants against viral infection. Monsanto Company & Washington University.

Bevan M (1984) Binary Agrobacterium vectors for plant transformation. Nucl Acids Res 12, 8711–8721.

Clerx-Van Haaster C M and Bishop D H L (1980) Analysis of the 3'-terminal RNA sequences of Snowshoe hare and Lacrosse Bunyaviruses, Virolology 105, 564–574.

Clerx-Van Haaster C M, Clerx J P M, Ushijima H. Akashi H, Fuller F and Bishop D H L (1982) Analysis of the 3'-terminal RNA sequences of Bunyaviruses and Nairoviruses (Bunyaviridae): evidence of end sequence generic differences within the virus family. J Gen Virol 61, 289–292.

Figurski D, Helinski D R (1979) Replication of an origin containing a derivative of plasmid $RK_2$ dependent on a plasmid function provided in trans. Proc Natl Acad Sci USA 76: 1648–1652.

Franck A, Guilley H, Jonard G, Richards K and Hirth L (1980) Cell 21, 285–294.

Grunstein J M and Hogness D S (1975) Colony hybridization: a method for the isolation of cloned DNAs that contain a specific gene. Proc Natl Acad Sci USA 72, 3961–3965.

Gubler U, Hoffman B J (11983) A simple and very efficient method for generating cDNA libaries. Gene 25, 263–269.

Hoekema A, Hirsch P R, Hooykaas P J J, Schilperoort R A (1983) A binary vector system based on separation of vir- and T-region of the *Agrobacterium tumefaciens* Ti-plasmid. Nature 303: 179–180.

Huynh T H, Young R A and David R W (1985) Construction and screening cDNA libaries in lambda gt10 and lambda gt11. In: DNA cloning techniques: a practical approach. (Glover D, ed.) IRL Press, Oxford, pp. 49–78.

Laemmli U K (1970) Cleavage of structural proteins during the assembly of the head of bacteriophage T4. Nature 244, 29–30.

Maniatis T, Fritsch E F, Sambrook J (1982) Molecular cloning, a laboratory manual. Cold Spring Harbor Laboratory, New York.

Murashige T, Skoog F (1962) A revised medium for rapid growth and bio-assays with tobacco tissue cultures. Physiol Plant 15: 473–497.

Tas P W L, Boerjan M L and Peters D (1977) The structural proteins of tomato spotted wilt virus. J Gen Virol 36, 81–91.

Towbin H, Staehelin T and Gordon J (1979) Electrophoretic transfer of proteins from polyacrylamide gels to nitrocellulose; procedure and some applications. Proc Natl Acad Sci USA 76, 4350–4354.

Van Grinsven M Q J M, Gielen J J L, Zethof J L A, Nijkamp H J J and Kool A J (1986) Transcriptional and post-transcriptional regulation of chloroplast gene expression in *Petunia hybrida*. Theor Appl Gen 73, 94–101.

Verkleij F N and Peters D (1983) Characterization of a defective form of tomato spotted wilt virus. J Gen Virol 64, 677–686.

Wieslander R (1979) A simple method to recover intact high molecular weight RNA and DNA after electrophoretic separation in low gelling temperature agarose gels. Anal Biochem 98, 305–309.

Yanish-Perron C; Vieria J and Messing J (1985) Improved M13 phage cloning vectors and host strains: nucleotide sequence of the M13MP18 and pUC19 vectors. Gene 33, 103–119.

What is claimed is:

1. Recombinant DNA constructs comprising a DNA sequence under expression control of a promoter and a terminator functioning in plants, which DNA sequence encodes an RNA sequence selected from the group consisting of:

(a) the S RNA nucleotide sequence from 1 to 2915 depicted in FIG. 4;

(b) the S RNA nucleotide sequence from 2763 to 1987 depicted in FIG. 4;

(c) the L RNA nucleotide sequence depicted in FIG. 6B;

(d) an RNA nucleotide sequence, encoding for a tospovirus protein, in which one or more codons of the RNA sequence of (a), (b) or (c) have been replaced by codons coding for the same amino acid or termination signal; and (e) an RNA sequence complementary to the RNA sequence of (a) (b), (c) or (d).

2. A construct according to claim 1 wherein the RNA sequence is the S RNA nucleotide sequence from 1 to 2915 depicted in FIG. 4.

3. A construct according to claim 1 wherein the RNA sequence is the S RNA nucleotide sequence from 198 to 2763 depicted in FIG. 4.

4. A construct according to claim 1 wherein the RNA sequence is the L RNA nucleotide sequence depicted in FIG. 6B.

5. A construct according to claim 1 wherein the RNA sequence encodes for a tospovirus protein in which one or more codons of the sequence of (a), (b) or (c) have been replaced by codons coding for the same amino acid.

6. The DNA construct of claim 1 wherein the promoter is a viral, fungal, bacterial, animal or plant derived promoter.

7. The DNA construct of claim 6 wherein the terminator is a viral, fungal, bacterial animal or plant derived terminator.

8. A plant comprising in its genome a DNA construct according to claim 1.

9. Plant material selected from the group consisting of protoplasts, plant cells, seeds and plantlets comprising in its genome a DNA construct according to claim 1.

10. A process of preparing genetically transformed plants comprising:

a) inserting into the genome of a plant cell a DNA construct of claim 1, b) obtaining transformed cells and c) regenerating genetically transformed plants from the transformed cells.

11. Recombinant DNA constructs capable of providing plants with resistance to infection by topsoviruses comprising a DNA sequence under expression control of a promoter and a terminator capable of functioning in plants, wherein the DNA sequence encodes an RNA sequence which is complementary to one which, when incubated for 16 hours in a buffer system comprising 5 times standard saline citrate, 0.5% sodium dodecyl sulphate, 5 times Denhardts solution, 50% formamide and 100 μg/ml carrier DNA followed by washing 3 times with a buffer system comprising 1 times standard saline citrate and 0.1% sodium dodecyl sulphate at 65° C. for one hour each time, still hybridizes with the sequence of (a), (b), (c), (d) or (e) of claim 1.

12. A construct according to claim 1 wherein the RNA sequence is an RNA sequence complementary to the RNA sequence of (a), (b), (c) or (d).

13. The DNA sequence of claim 1 wherein the promoter is a plant derived promoter.

14. A construct according to claim 11 wherein the promoter is a viral, fungal, bacterial, animal or plant derived promoter.

15. A construct according to claim 14 wherein the promoter is a plant derived promoter.

16. A plant comprising in its genome a DNA construct according to claim 11.

* * * * *